United States Patent [19]

Shibasaki et al.

[11] Patent Number: 4,632,997
[45] Date of Patent: Dec. 30, 1986

[54] METHOD FOR PREPARING CIS-BICYCLO[3.3.0]OCTYLIDENE DERIVATIVE

[75] Inventors: Masakatsu Shibasaki, Tokyo; Mikiko Sodeoka; Yuji Ogawa, both of Sagamihara, all of Japan

[73] Assignee: Sagami Chemical Research Center, Tokyo, Japan

[21] Appl. No.: 700,003

[22] Filed: Feb. 8, 1985

[30] Foreign Application Priority Data

Feb. 10, 1984 [JP] Japan ................................. 59-22011
Mar. 28, 1984 [JP] Japan ................................. 59-58457

[51] Int. Cl.$^4$ ..................... C07C 51/36; C07C 67/303; C07D 309/10; C07F 7/18
[52] U.S. Cl. .................................... 549/214; 549/415; 549/421; 549/423; 556/437; 560/107; 560/116; 560/119; 560/139; 562/498; 562/501
[58] Field of Search ............... 560/119, 107, 116, 139; 562/501, 498; 549/415, 421, 423, 214; 556/437

[56] References Cited

U.S. PATENT DOCUMENTS 3,736,335  5/1983  Wendler et al. ................. 560/119 X

OTHER PUBLICATIONS

Mase et al., Tetrahedron Letters, vol. 25, No. 44, pp. 5087–5090, 1984.
Morrison et al., "Organic Chemistry", Third Edition, Chapter 23, Amines II. Reactions, pp. 758–760 and 1147.
Tsutsui et al., "Introduction to Metal π-Complex Chemistry", Chapter 1, History, Classification, and Nomenclature, 1970, pp. 1-2 & 8–10.
A. Merriam-Webster, "Webster's Third New International Dictionary", vol. II, 1966, p. 1108.
Encyclopaedia Chemica, pp. 348–349, vol. 5.

Primary Examiner—Natalie Trousof
Assistant Examiner—Patricia M. Scott
Attorney, Agent, or Firm—Schwartz, Jeffery, Schwaab, Mack, Blumenthal & Evans

[57] ABSTRACT

A method for preparing a cis-bicyclo[3.3.0]octylidene derivative represented by the formula:

wherein $R^1$ is a hydrogen atom or an alkyl group; $R^2$ is a hydrogen atom or a protective group for hydroxyl group; and Y is $$-CH_2OR^3 \text{ or } -X-\underset{\underset{OR^3}{|}}{CH}-R^4;$$

where $R^3$ is a hydrogen atom or a protective group for hydroxyl group; $R^4$ is a hydrogen atom or a straight, branched or cyclic alkyl group, alkenyl group or alkynyl group; and X is a group represented by CH=CH or C≡C, comprises carrying out the catalytic hydrogenation reaction of a (1-alkenyl)-cis-bicyclo[3.3.0]octene derivative represented by the formula:

wherein $R^1$, $R^2$ and Y have the same meanings as defined above,
in the presence of a metal carbonyl compound or its complex represented by the formula:

$$M_w(CO)_x(H)_y(R)_z$$

wherein M is a metal element of the group VIB; R is a π ligand or a phosphine ligand; w is 1 or 2; x is an integer of 3 to 6; y is 0 or 1; and z is 0 or an integer of 1 to 3.

9 Claims, No Drawings

METHOD FOR PREPARING CIS-BICYCLO[3.3.0]OCTYLIDENE DERIVATIVE

BACKGROUND OF THE INVENTION

This invention relates to a cis-bicyclo[3.3.0]octylidene derivative represented by the formula:

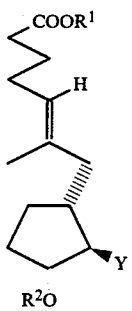

wherein $R^1$ is a hydrogen atom or an alkyl group; $R^2$ is a hydrogen atom or a protective group for hydroxyl group; and Y is

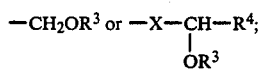

where $R^3$ is a hydrogen atom or a protective group for hydroxyl group; $R^4$ is a hydrogen atom or a straight, branched or cyclic alkyl group, alkenyl group or alkynyl group; and X is a group represented by CH=CH or C≡C.

The cis-bicyclo[3.3.0]octylidene derivative represented by the above formula (I) obtained according to this invention can be subjected to deprotection of the primary hydroxyl group, oxidation, elongation of an ω-chain by utilizing the Wittig reaction and reduction of a 15-position carbonyl group (prostaglandine numbering) for deprotection, or deprotection of the protective group and hydrolysis of the ester to be led to a carbacycline which is useful as a therapeutic or prophylactic of various circulatory diseases (see Reference examples shown below).

In the prior art, most of the methods for preparation of a 5-E-exo-trisubstituted olefin such as a cis-bicyclo[3.3.0]octylidene derivative represented by the above formula (I) utilize the Wittig reaction as shown below, and they are disclosed in, for example, M. Shibasaki, J. Ueda and S. Ikegami, Tetrahedron Lett., 433 (1979); D. R. Morton, Jr. and F. C. Brokaw, J. Org. Chem., 44, 2880 (1979); W. Skuballa and H. Vorbrüggen, Angew. Chem. Int. Ed. Engl., 20, 1046 (1981); Y. Konishi, M. Kawamura, Y. Iguchi, Y. Arai and M. Hayashi, Tetrahedron, 37, 4391 (1981); etc. However, in these cases, a mixture of 5-E isomer and 5-Z isomer is obtained as shown in the following reaction scheme and it is very difficult under the present situation to separate only the 5-E isomer useful as a pharmaceutical from such a mixture.

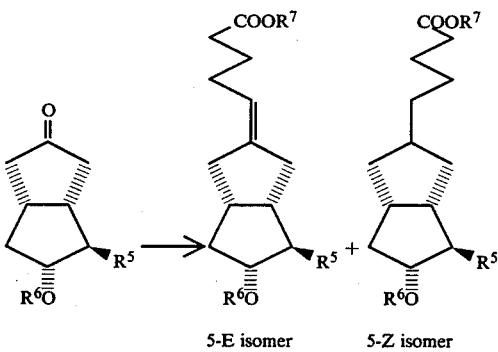

5-E isomer     5-Z isomer

SUMMARY OF THE INVENTION

The present inventors have made investigations in order to overcome the drawback of the prior art and found that the cis-bicyclo[3.3.0]octylidene derivative represented by the above formula (I) can be obtained stereospecifically to accomplish this invention.

It would not be exaggerating to say that synthesis of carbacyclines has been rendered very easy, and it is certain that developments of carbacyclines which have been passed up due to the difficulty in synthesis will extend to the development of pharmaceuticals for oral administration.

The present invention produces stereospecifically a cis-bicyclo[3.3.0]octylidene derivative represented by the above formula (I) by carrying out the catalytic hydrogenation reaction of a (1-alkenyl)-cis-bicyclo[3.3.0]octene derivative represented by the formula:

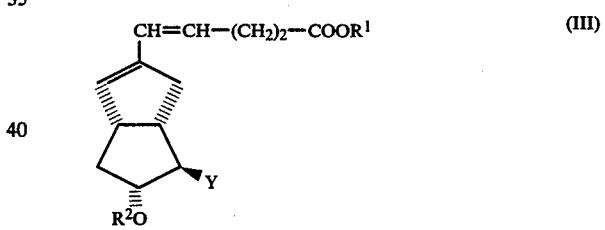

wherein $R^1$ is a hydrogen atom or an alkyl group; $R^2$ is a hydrogen atom or a protective group for hydroxyl group; and Y is

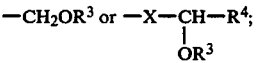

where $R^3$ is a hydrogen atom or a protective group for hydroxyl group; $R^4$ is a hydrogen atom or a straight, branched or cyclic alkyl group, alkenyl group or alkynyl group; and X is a group represented by CH=CH or C≡C,
in the presence of a metal carbonyl compound or its complex represented by the formula:

wherein M is a metal element of the group VI B; R is a π ligand or a phosphine ligand; w is 1 or 2; x is an integer of 3 to 6; y is 0 or 1; and z is 0 or an integer of 1 to 3.

The (1-alkenyl)-cis-bicyclo[3.3.0]octene derivative represented by the above formula (III), which is the starting material in this invention, is a compound which can very efficiently be derived from a Corey lactone (see Pre-text in 104th Anniversary of Society of Pharmacology of Japan, p. 282, and Reference example shown below). In the compounds obtainable according to this method, $R^1$ in the above formula may be a hydrogen atom, a methyl group, an ethyl group, a propyl group, an isopropyl group, a butyl group, an isobutyl group, a sec-butyl group, a t-butyl group, a pentyl group, a hexyl group, a heptyl group, an octyl group, etc.; $R^2$ and $R^3$ may be a hydrogen atom, a tetrahydropyranyl group, a t-butyldimethylsilyl group, a 1-ethoxyethyl group, a diphenyl-t-butylsilyl group, a methoxymethyl group, a 1-methyl-1-methoxyethyl group, a 4-methoxytetrahydropyranyl group, a methyl group, a benzyl group, a benzoyl group, an acetyl group, a $\beta$-methoxyethoxymethyl group, a triethylsilyl group, etc.

More specifically, there may be included {3-(4'-methoxycarbonyl-1'-butenyl)-6(S)-(3'(S)-hydroxy-4'(RS)-methyl-trans- 1'-octen-6'-ynyl)-7(R)-hydroxy-(1S,5S)-cis-bicyclo[3.3.0]oct-2-ene}, {3-(4'-methoxycarbonyl-1'-butenyl)-6(S)-(3'(S)-t-butyldimethylsilyloxy-4'-(RS)-methyl-trans-1'-octen-6'-ynyl)-7(R)-t-butyldimethylsilyloxy-(1S,5S)-cis-bicyclo[3.3.0]oct-2-ene}, {3-(4'-methoxycarbonyl-1'-butenyl)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.0]oct-2-ene}, {3-(4'-ethoxycarbonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene}, {3-(4'-methoxycarbonyl-1'-butenyl)-6(S)-(3'(S)-t-butyldimethylsilyloxy-5'(R)-methyl-trans-1'-decen-8'-enyl)-7(R)-t-butyldimethylsilyloxy-(1S, 5S)-cis-bicyclo[3.3.0]oct-2-ene}, {3-(4'-methoxycarbonyl-1'-butenyl)-6(S)-(3'(S)-tetrahydropyranyloxy-5'(R)-methyl-trans-1'-decen-8'-enyl)-7(R)-tetrahydropyranyloxy-(1S, 5S)-cis-bicyclo[3.3.0]oct-2-ene}, {3-(4'-ethoxycarbonyl-1'-butenyl)-6(S)-(3'(S)-t-butyldimethylsilyloxy-5'(R)-methyl-trans-1'-decen-8'-enyl)-7(R)-t-butyldimethylsilyloxy-(1S,5S)-cis-bicyclo[3.3.0]oct-2-ene}, {3-(4'-methoxycarbonyl-1'-butenyl)-6(S)-(3'(S)-t-butyldimethylsilyloxy-3 '-cyclopentyl-trans-1'-propenyl)-7(R)-t-butyldimethylsilyloxy-(1S,5S)-cis-bicyclo[3.3.0]oct-2-ene}, {3-(4'-methoxycarbonyl-1'-butenyl)-6(S)-(3'(S)-tetrahydropyranyloxy-3'-cyclopentyl-trans-1'-propenyl)-7(R)-tetrahydropyranyloxy-(1S,5S)-cis-bicyclo-[3.3.0]oct-2-ene}, {3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2ene-}, {3-(4'-ethoxycarbonyl-1'-butenyl)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]oct-2-ene}, {3-(4'-methoxycarbonyl-1'-butenyl)-6(S)-(3'(S)-t-butyldimethylsilyloxy-trans-1'-octenyl)-7(R)-t-butyldimethylsilyloxy-(1,5S)-cis-bicyclo[3.3.0]oct-2-ene}, {3-(4'-methoxycarbonyl-1'-butenyl)-6(S)-(3'-t-butyldimethylsilyloxy-trans-1'-octenyl)-7(R)-t-butyldimethylsilyloxy-(1S,5S)-cis-bicyclo[3.3.0]oct-2-ene}, {3-(4'-methoxycarbonyl-1'-butenyl)-6(S)-(3'(S)-t-butyldimethylsilyloxy-4'(S)-methyl-1'-octynyl-7(R)-t-butyldimethylsilyloxy-( 1S,5S)-cis-bicyclo[3.3.0]oct-2-ene} and the like.

In this invention, it is essentially required to carry out the catalytic hydrogenation reaction in the presence of a metal carbonyl compound or its complex represented by the above formula (II). Most of the metal carbonyl compounds or complexes thereof represented by the above formula (II) are commercially available, but they can easily be prepared, if necessary (see M. F. Farona in Organometallic Reactions and Synthesis, Vol. 6, E. I. Becker and M. Tsutsui, Ed., Plenum Press, New York and London, 1977, p. 223).

In the above formula (II), the $\pi$ ligand represented by R is a ligand as exemplified by benzene, toluene, thiophene, pyridine, anisole, chlorobenzene, methyl benzoate, cyclopentadienyl, cyclopentadienylmethyl, cycloheptatriene, cyclooctatriene, mesitylene, stilbene, acetophenone, azulene, cyclooctadiene, 1,2-diphenylethane, diphenylmethane, biphenyl, 1,4-diphenylbutadiene, phenanthrene, 1,4-diphenyl-2,3-diethoxycarbonyl-2,5-cyclohexadiene, acetonitrile, hexamethylbenzene, 3-carbomethoxyanisole, benzophenone, bicyclo[2.2.1-]hepta-2,5-diene, naphthalene, anthracene and the like.

Specific examples of the metal carbonyl compound or its complex represented by the above formula (II) to be used in this invention may include hexacarbonyl chromium, benzenetricarbonyl chromium, toluenetricarbonyl chromium, thiophenetricarbonyl chromium, pyridinetricarbonyl chromium, anisoletricarbonyl chromium, chlorobenzenetricarbonyl chromium, methylbenzoatetricarbonyl chromium, hydridocyclopentadienyltricarbonyl chromium, cyclopentadienylmethyltricarbonyl chromium, cycloheptatrienetricarbonyl chromium, cyclooctatrienetricarbonyl chromium, mesitylenetricarbonyl chromium, stilbene-bis-tricarbonyl chromium, acetophenonetricarbonyl chromium, naphthalenetricarbonyl chromium, anthracenetricarbonyl chromium, benzenetricarbonyl molybdenum, mesitylenetricarbonyl molybdenum, pyridinetricarbonyl molybdenum, azulene-bistricarbonyl molybdenum, cycloheptatrienetricarbonyl molybdenum, cyclooctatrienetricarbonyl molybdenum, dicyclopentadienyl-bis-tricarbonyl dimolybdenum, hydridocyclopentadienyltricarbonyl molybdenum, benzenetricarbonyl tungsten, toluenetricarbonyl tungsten, pyridinepentacarbonyl tungsten, cyclooctadienetetracarbonyl tungsten, mesitylenetricarbonyl tungsten, 1,2-diphenylethanetricarbonyl chromium, diphenylmethanetricarbonyl chromium, 1,2-diphenylethane-bis-tricarbonyl chromium, diphenylmethane-bis-tricarbonyl chromium, biphenyl-bis-tricarbonyl chromium, 1,4-diphenylbutadiene-bis-tricarbonyl chromium, phenanthrenetricarbonyl chromium, tris-acetonitriletricarbonyl chromium, 1,4-diphenyl-2,3-diethoxycarbonyl-2,5-cyclohexadiene-bis-tricarbonyl chromium, bicyclo[2.2.1]hepta-2,5-dienetetracarbonyl molybdenum, triphenylphosphinepentacarbonyl chromium and so on.

The metal carbonyl compound or its complex represented by the above formula (II) may be used in an amount of $10^{-5}$ to 20% by weight based on the (1-alkenyl)-cis-bicyclo[3.3.0]octene derivative, whereby the reaction can proceed smoothly.

The pressure of hydrogen in carrying out the catalytic hydrogenation reaction of this invention may be generally atmospheric to 150 atm., but preferably 30 to 100 atm. in view of the reaction efficiency and operating procedures. The reaction should be conducted desirably in a solvent, which may be one or a combination of two or more organic media selected from the group consisting of acetone, 2-butanone, 2-pentanone, 3-pentanone, acetonitrile, or halogenated hydrocarbons such as methylene chloride, chloroform, carbon tetrachloride, dichloroethane, etc., aromatic organic solvents such as benzene, toluene, chlorobenzene, bromobenzene, dichlorobenzene, dibromobenzene, etc., aliphatic hydrocarbons such as pentane, hexane, heptane, cyclopentane, cyclohexane, decalin, etc., esters such as ethyl formate, ethyl acetate, methyl propionate, ethyl propionate, etc., alcohols such as methanol, ethanol, propanol, butanol, ethylene glycol, propylene glycol, glycerine, benzyl alcohol, phenylethyl alcohol, tetrahydrofuran, etc.

The reaction can proceed at room temperature to 200° C., but the reaction temperature may differ depending on other conditions. When a metal carbonyl compound is used, it has been known in the art to carry out frequently the reaction while irradiating a light in the longer wavelength region of UV-ray for the purpose of revelation or enhancement of the catalytic activity of such a kind of compound. Such a method can of course be utilized in practicing this invention.

This invention is described in more detail by referring to the following Examples and Reference examples.

REFERENCE EXAMPLE 1

{1-2-Oxa-3-oxo-6-exo-t-butyldimethylsilyloxymethyl-7-endo-tetrahydropyranyloxybicyclo[3.3.0]octane} (2.22 g, 6 mmol) was dissolved in toluene (10 ml) under argon gas atmosphere, and the solution was cooled to $-75°$ C. To the solution was added diisobutylaluminum hydride (25 g/100 ml hexane solution; 5.1 ml, 9 mmol) and the mixture was stirred at $-75°$ C. for 70 minutes. Methanol was added at $-75°$ C. until generation of hydrogen had not been admitted and the temperature of the mixture was raised to room temperature. After the mixture was diluted with ethyl acetate (130 ml), washed with a saturated saline solution (20 ml×4 times). The mixture was dried with anhydrous magnesium sulfate, and distilled out the solvents to obtain {1-2-oxa-3-hydroxy-6-exo-t-butyldimethylsilyloxymethyl-7-endo-tetrahydropyranyloxybicyclo[3.3.0]octane} (2.33 g, Yield: 100%).

IR (neat): 3430, 2950, 2860, 835 cm$^{-1}$.

NMR δ (CDCl$_3$): 5.70–5.30 (m, 1H), 4.85–4.55 (m, 2H), 4.40–3.25 (m, 5H), 0.90 (s, 9H).

Mass m/z (%): 213 (5), 159 (17), 85 (100), 75 (19), 73 (13).

$[\alpha]_D^{20} = -28°$ (c=1.98, MeOH).

REFERENCE EXAMPLE 2

Potassium t-butoxide (3.16 g, 28.2 mmol) was dissolved in THF (50 ml) under argon gas atmosphere. To the solution was added at room temperature methyltriphenylphosphonium bromide (10.07 g, 28.2 mmol) which was previously dried enough at 100° C. under reduced pressure. After 5 minutes stirring, to the mixture was added (1-2-oxa-3-hydroxy-6-exo-t-butyldimethylsilyloxymethyl-7-endo-tetrahydropyranyloxybicyclo[3.3.0]octane} (3.40 g, 9.1 mmol) in THF solution (30 ml) and the mixture was stirred at room temperature for 20 minutes. After a saturated aqueous ammonium chloride solution was added to the mixture, THF was distilled out therefrom under reduced pressure. The resultant aqueous layer was extracted with ether and the extract was washed with a saturated saline solution. After dryness with anhydrous magnesium sulfate, ether was distilled out. The residue was purified through silica gel column chromatography (ether:n-hexane=2:3) to obtain {d-2α-allyl-3β-t-butyldimethylsilyloxymethyl-4α-tetrahydropyranyloxy-1α-cyclopentanol} (3.18 g, 94%).

IR (neat): 3500, 2950, 2870, 1640, 835 cm$^{-1}$.

NMR δ (CDCl$_3$): 5.80 (m, 1H), 5.00 (m, 2H), 4.65 (bs, 1H), 4.30–3.00 (m, 6H), 0.90 (s, 9H).

Mass m/z (%): 285 (1), 229 (1), 211 (3), 159 (26), 85 (100), 75 (21), 73 (13).

$[\alpha]_D^{20} = +21°$ (c=2.44, MeOH).

REFERENCE EXAMPLE 3

In methylene chloride (40 ml) was dissolved {d-2α-allyl-3β-t-butyldimethylsilyloxymethyl-4α-tetrahydropyranyloxy-1α-cyclopentanol} (3.16 g, 8.5 mmol) and then sodium acetate (280 mg, 2.6 mmol) and Celite (3.36 g) were added thereto. To the resultant mixture was added, under argon gas atmosphere at 0° C., pyridinium chlorochromate (3.68 g, 17.1 mmol) and stirred at 0° C. for 18 hours. The reaction mixture was diluted with ether and purified through florisil column chromatography (ether:n-hexane=1:3 to 3:1) to obtain {1-2α-allyl-3βα-t-butyldimethylsilyloxymethyl-4α-tetrahydropyranyloxy-1-cyclopentanone} (2.82 g, Yield: 90%).

IR (neat): 2950, 2880, 1748, 1642, 840 cm$^{-1}$.

NMR δ (CDCl$_3$): 5.70 (m, 1H), 5.03 (d, J=17 Hz, 1H), 5.00 (d, J=11 Hz, 1H), 4.65 (bs, 1H), 4.30 (m, 1H), 3.30–4.00 (m, 4H), 0.90 (s, 9H).

Mass m/z (%): 209 (17), 159 (17), 85 (100), 75 (35), 73 (23), 41 (17).

$[\alpha]_D^{20} = -55°$ (c=2.19, MeOH).

REFERENCE EXAMPLE 4

{1-2α-Allyl-3β-t-butyldimethylsilyloxymethyl-4α-tetrahydropyranyloxy-1-cyclopentanone} (2.79 g, 7.57 mmol) was dissolved in methylene chloride (26 ml) and to the solution was added a zinc-titanium chloride-methylene bromide reagent (Zn-TiCl$_4$-CH$_2$Br$_2$/THF, 46 ml) at room temperature. After disappearance of the starting materials had been confirmed by using TLC, the reaction mixture was poured into a mixed solution of saturated aqueous sodium hydrogencarbonate solution (500 ml) and ether (500 ml). After the ether layer was separated from the mixture, the aqueous layer was further extracted with ether. The ether layers were combined, and the mixture was washed with a saturated saline solution, dried over anhydrous magnesium sulfate and evaporated out the solvents. The residue was purified through silica gel column chromatography (ether:n-hexane=1:10) to obtain {1-2α-allyl-3β-t-butyldimethylsilyloxymethyl-4α-tetrahydropyranyloxy-1-cyclopentylidene} (2.48 g, Yield: 90%).

IR (neat): 2950, 2870, 1660, 1640, 835 cm$^{-1}$.

NMR δ (CDCl$_3$): 5.60 (m, 1H), 4.75–5.20 (m, 4H), 4.63 (bs, 1H), 3.30–4.30 (m, 5H), 0.90 (s, 9H).

Mass m/z (%): 159 (18), 133 (11), 85 (100), 75 (19), 73 (13).

$[\alpha]_D^{20} = -43°$ (c=2.84, MeOH).

REFERENCE EXAMPLE 5

9-Borabicyclo[3.3.1]nonane (dimer, 2.472 g, 20.3 mmol) was suspended in THF (28 ml) under argon gas atmosphere. A solution of {1-2α-allyl-3β-t-butyldimethylsilyloxymethyl-4α-tetrahydropyranyloxy-1-cyclopentylidene} (2.476 g, 6.75 mmol) dissolved in THF (45 ml) was added dropwise to the aforesaid suspension under ice-cooling, and the mixture was stirred at 5 to 10° C. for 7.5 hours. To the mixture were added a 6N aqueous sodium hydroxide solution (13.5 ml, 81 mmol) and a 30% aqueous hydroperoxide solution (11.5 ml, 101.3 mmol) and stirred at 60° C. for 1.5 hours. After evaporation of THF under reduced pressure, the resultant mixture was extracted with ethyl acetate. The separated organic layer was washed successively with an aqueous sodium thiosulfate solution and a saturated saline solution. The thus treated mixture was dried over anhydrous magnesium sulfate and then distilled out the solvents. The residue was purified through silca gel column chromatography (ether:methanol=40:1) to obtain {d-1α-hydroxymethyl-2α-(3-hydroxypropyl)-3β-t-butyldimethylsilyloxymethyl-4α-tetrahydropyranyloxycyclopentane} (2.65 g, Yield: 97%).

IR (neat): 3400, 2940, 2860, 835 cm$^{-1}$.

NMR δ (CDCl$_3$) 4.65 (bs, 1H), 4.10 (m, 1H), 3.15–3.95 (m, 8H), 0.90 (s, 9H).

Mass m/z (%): 159 (19), 149 (18), 133 (19), 121 (13), 105 (15), 93 (10), 91 (10), 85 (100), 79 (11), 75 (34), 73 (18), 67 (17), 57 (24), 55 (16), 43 (17), 41 (21).

$[\alpha]_D^{20} = +2°$ (c=1.65, MeOH).

REFERENCE EXAMPLE 6

Oxalyl chloride (1.88 ml, 20.0 mmol) was dissolved in 55 ml of methylene chloride at −60 °C. under argon gas atmosphere. To the solution was added a solution of dimethyl sulfoxide (3.39 ml, 47.7 mmol) dissolved in methylene chloride (15 ml). After the mixture was stirred at −60° C. for 20 minutes, a solution of {d-1α-hydroxymethyl-2α-(3-hydroxypropyl)-3β-t-butyldimethylsilyloxymethyl-4α-tetrahydropyranyloxycyclopentane} (1.48 g, 3.67 mmol) dissolved in methylene chloride (30 ml) was added thereto. After the mixture was stirred at −60° C. for 20 minutes, triethylamine (15.36 ml, 110.1 mmol) was added thereto and the temperature of the mixture was raised to room temperature. Water was poured into the mixture and the mixture was extracted with methylene chloride. The separated organic layer was washed with an aqueous saline solution and dried over anhydrous magnesium sulfate. Evaporation of the solvent to obtain {2-hydroxy-3-formyl-6-exo-t-butyldimethylsilyloxymethyl-7-endo-tetrahydropyranyloxybicyclo[3.3.0]octane} (1.19 g, Yield: 81%). According to spectrum data, this compound was equilibrium mixtures between β-hydroxyaldehyde and lactol.

IR (KBr): 3450, 2950, 2870, 2750, 1730, 835 cm$^{-1}$.

NMR δ (CDCl$_3$): 9.75 (trace), 4.65 (m, 1H), 3.10–4.50 (m, 6H), 0.90 (s, 9H).

Mass m/z (%): 313 (trace, M$^+$ −85), 159 (15), 85 (100), 75 (17), 73 (12), 57 (12), 47 (11).

REFERENCE EXAMPLE 7

{2-Hydroxy-3-formyl-6-exo-t-butyldimethylsilyloxymethyl-7-endo-tetrahydropyranyloxybicyclo[3.3.0]octane} (1.19 g, 2.97 mmol) was dissolved in benzene (4.5 ml). To the solution was added dimethylammonium trifluoroacetate (1.14 g, 3.66 mmol) under argon gas atmosphere and the mixture was stirred at 50° to 70° C. for 16 hours. After the reaction mixture was allowed to stand for cooling, water (50 ml) was added thereto and the mixture was extracted with ether. After an ether layer was separated, the ether layer was washed successively with a saturated aqueous sodium ammonium chloride solution, a saturated aqueous sodium hydrogencarbonate solution and water. The ether layer was dried over anhydrous magnesium sulfate and then evaporation of the solvent was carried out. The residue was purified through silica gel column chromatography (ether:n-hexane=1:1) to obtain {1-3-formyl-6-exo-t-butyldimethylsilyloxymethyl-7-endo-tetrahydropyranyloxybicyclo[3.3.0]oct-2-ene} (1.03 g, 82%).

IR (neat): 2950, 2870, 1680, 1620, 835 cm$^{-1}$.

NMR δ (CDCl$_3$) 9.78 (s, 1H), 6.71 (d, J=2Hz, 2H), 4.60 (bs, 1H), 3.00–4.20 (m, 6H), 0.90 (s, 9H).

Mass m/z (%): 295 (1), 159 (33), 85 (100), 75 (26), 73 (19), 67 (12), 57 (14), 45 (14), 43 (22).

$[\alpha]_D^{20} = -77°$ (c=2.77, MeOH).

REFERENCE EXAMPLE 8

3-Carboxypropyltriphenylphosphonium bromide (5.58 g, 13 mmol) was suspended in THF (60 ml) under argon gas atmosphere. To the solution was added a solution of potassium t-butoxide (3.01 g, 26 mmol) in THF (50 ml) and the mixture was stirred at room temperature for 10 minutes. To the mixture was added dropwise a solution of {1-3-formyl-6-exo-t-butyldimethylsilyloxymethyl-7-endo-tetrahydropyranyloxybicyclo[3.3.0]oct-2-ene} (990 mg, 2.6 mmol) in THF (20 ml) and the miture was stirred at room temperature for 30 minutes. To the mixture was added a saturated aqueous ammonium chloride solution and THF was distilled out under reduced pressure. The resultant aqueous layer was adjusted to pH 5 to 4 with a 10% aqueous hydrochloric acid solution and extracted with ethyl acetate. The separated organic layer was dried over anhydrous magnesium sulfate and then solvents were distilled out. To the residue was added ether, and insolubles were removed by filtration. To the filtrate was added an ether solution of diazomethane. After disappearance of spot of [3-(4-carboxy-1-butenyl)-6-exo-t-butyldimethylsilyloxymethyl-7-endo-tetrahydropyranyloxybicyclo[3.3.0]oct-2-ene]was confirmed by using thin layer chromatography, to the mixture was added a small amount of formic acid and the mixture was immediately washed with a saturated aqueous sodium hydrogencarbonate solution and a saturated saline solution. The resultant mixture was dried over anhydrous magnesium sulfate and was distilled out the solvents. The residue was purified through silica gel column chromatography (ether:n-hexane=1:2) to obtain {1-3-(4-methoxycarbonyl-1-butenyl)-6-exo-t-butyldimethylsilyloxymethyl-7-endo-tetrahydropyranyloxybicyclo[3.3.0]oct-2-ene} (1.09 g, Yield 90%). The ratio of (Z)-isomer and (E)-isomer was 2:1.

IR (neat): 2950, 2870, 1745, 840 cm$^{-1}$.

NMR δ (CDCl$_3$): 6.24 (d, J=16 Hz, ⅓trans), 5.98 (d, J=11 Hz, ⅔H, cis), 5.57 (bs, 1H), 5.30 (m, 1H), 4.60 (bs, 1H), 3.20–4.25 (m, 8H), 2.95 (1H), 0.90 (s, 9H).

Mass m/z (%): 464 (trace, M$^+$), 323 (20), 231 (28), 159 (29), 157 (16), 117 (11), 85 (100), 75 (25), 73 (20), 67 (12), 57 (14), 43 (13), 41 (13).

$[\alpha]_D^{20} = -50°$ (c=1.36, MeOH).

REFERENCE EXAMPLE 9

The same procedures were carried out as in Reference example 8 except that {1-3-formyl-6-exo-t-butyldimethylsilyloxymethyl-7-endo-tetrahydropyranyloxybicyclo[3.3.0]oct-2-ene} (495 mg, 1.3 mmol) was employed as a starting material to yield {3-(4-carboxy-1-butenyl)-6-exo-t-butyldimethylsilyloxymethyl-7-endo-tetrahydropyranyloxybicyclo[3.3.0]oct-2-ene} (0.55 g, Yield: 90%) as a colorless oily product.

IR (neat): 3400, 1710, 840 cm$^{-1}$. NMR δ (CDCl$_3$) 6.24 (d, J=16 Hz, ⅓trans), 5.95 (d, J=11 Hz, ⅔H, cis), 5.55 (bs, 1H), 5.30 (m, 1H), 4.60 (bs, 1H), 3.20–4.25 (m, 5H), 2.95 (m, 1H), 0.90 (s, 9H).

Mass m/z (%): 450 (M$^+$), 309, 265, 85.

REFERENCE EXAMPLE 10

The same procedures were carried out as in Reference examples 1 to 8 except that {2-oxa-3-oxo-6-exo-(1-methyl-1-methoxyethyloxymethyl-7-endo-tetrahydropyranyloxybicyclo[3.3.0]octane} (1.11 g, 3.38 mmol) was employed as a starting material to yield {1-3-(4-methoxycarbonyl-1-butenyl)-6-exo-(1-methyl-1-methoxyethyloxymethyl)-7-endo-tetrahydropyranyloxybicyclo[3.3.0]oct-2-ene} (570 mg, Over all yield: 40%) as a colorless oily product.

IR (neat): 2950, 1742 cm$^{-1}$. NMR δ (CDCl$_3$): 6.22 (d, J=16 Hz, ⅓trans), 5.95 (d, J=11 Hz, ⅔H, cis), 5.58 (bs, 1H), 5.30 (m, 1H), 4.62 (m, 1H), 3.67 (s, 3H), 3.25–4.10 (m, 5H), 3.20 (s, 3H), 3.00 (m, 1H), 1.34 (s, 6H).

Mass m/z (%): 390, 350, 338, 332, 306, 248, 191, 143, 131, 117, 91, 86, 85, 79, 73, 67.

$[\alpha]_D^{20} = -43.5°$ (c=0.718, MeOH).

REFERENCE EXAMPLE 11

The same procedures were carried out as in Reference examples 1 to 8 except that {2-oxa-3-oxo-6-exo-(t-butyldimethylsilyloxymethyl-7-endo-(1-methyl-1-methoxyethyloxy)-bicyclo[3.3.0]octane} (1.21 g, 3.38 mmol) was employed as a starting material to yield {1-3-(4-methoxycarbonyl-1-butenyl)-6-exo-t-butyldimethylsilyloxymethyl-7-endo-(1-methyl-1-methoxyethyloxy)-bicyclo[3.3.0]oct-2-ene} (570 mg, Over all yield: 37%) as a colorless oily product.

IR (neat): 2960, 1745, 838 cm$^{-1}$.

NMR δ (CDCl$_3$): 6.24 (d, J=15 Hz, ⅓trans), 5.96 (d, J=11 Hz, ⅔H, cis), 5.60 (bs, 1H), 5.30 (m, 1H), 3.68 (s, 3H), 3.30–4.30 (m, 3H), 3.20 (s, 3H), 3.00 (m, 1H), 1.33 (s, 6H), 0.90 (s, 9H), 0.05 (s, 6H).

Mass m/z (%): 420, 380, 363, 323, 231, 171, 157, 115, 89, 75, 73.

$[\alpha]_D^{20} = -21°$ (c=0.592, MeOH).

EXAMPLE 1

{1-3-(4-Methoxycarbonyl-1-butenyl)-6-exo-t-butyldimethylsilyloxymethyl-7-endo-tetrahydropyranyloxybicyclo[3.3.0]oct-2-ene} (mixture of cis:trans =2:1; 116 mg, 0.25 mmol) and methylbenzoatetricarbonyl chromium (14 mg, 0.05 mmol) were dissolved in acetone (10 ml) and a cycle of cooling-diminished pressure-dissolution by using liquid nitrogen were repeated to degas. The resultant mixture was transferred into 100 ml of autoclave and 70 kg/cm$^2$ of hydrogen gas was charged therein. After completion of the reaction at 120° C. for 15 hours, evaporation of the solvent followed by purification through silica gel column chromatography (ether:n-hexane=1:5) were carried out to obtain {3E-(4-methoxycarbonylbutylidene)-6-exo-t-butyldimethylsilyloxymethyl-7-endo-tetrahydropyranyloxybicyclo[3.3.0]octane} (111 mg, Yield: 95%). The obtained product did not contain a Z-isomer at all with regard to a double bond from the result of the analysis by using a gas chromatography.

IR (neat): 2970, 2880, 1747, 840 cm$^{-1}$.

NMR δ (CDCl$_3$) 5.23 (t, J=7 Hz, 1H), 4.66 (m, 1H), 3.70 (s, 3H), 3.30–4.10 (m, 5H), 0.90 (s, 9H), 0.05 (s, 6H).

Mass m/z (%): 466 (M$^+$, trace), 325 (37), 233 (70), 201 (44), 159 (100), 85 (100), 75 (75), 73 (65), 67 (43), 57 (40).

EXAMPLE 2

{1-3-(4-Methoxycarbonyl-1-butenyl)-6-exo-t-butyldimethylsilyloxymethyl-7-endo-tetrahydropyranyloxybicyclo[3.3.0]oct-2-ene} (113 mg, 0.24 mmol) and toluenetricarbonyl chromium (14 mg, 0.05 mmol) were dissolved in acetone (10 ml), degassed and then charged into 100 ml of autoclave. Under 70 kg/cm$^2$ of hydrogen gas pressure, the reaction was carried out at 130° C. for 13 hours. Evaporation of the solvent followed by purification through silica gel column chromatography (ether:n-hexane=1:5) afforded {3E-(4-methoxycarbonylbutylidene)-6-exo-t-butyldimethylsilyloxymethyl-7-endo-tetrahydropyranyloxybicyclo[3.3.0]octane} (92 mg, Yield: 81%). The spectrum data of the obtained product are completely agreed with those of the compound obtained in Example 1. From the results of the analysis by using a gas chromatography, the product did {1-3-(4-Methoxycarbonyl-1-butenyl)-6-exo-t-butyldimethylsilyloxymethyl-2-ene} (116 mg, 0.25 mmol) and methylbenzoatetricarbonyl chromium (14 mg, 0.05 mmol) were dissolved in acetonitrile (10 ml), degassed and then charged into 100 ml of autoclave. Under 70 kg/cm$^2$ of hydrogen gas pressure, the reaction was carried out at 130° C. for 12 hours. Evaporation of the solvent followed by purification through silica gel column chromatography (ether:n-hexane=1:5) afforded {3E-(4-methoxycarbonylbutylidene)-6-exo-t-butyldimethylsilyloxymethyl-7-endo-tetrahydropyranyloxybicyclo[3.3.0]octane} (30 mg, Yield: 26%). The spectrum data of the obtained product are completely agreed with those of the compound obtained in Example 1. From the results of the analysis by using a gas chromatography, the product did not contain a Z-isomer at all. Other than the above, cis-isomer which is used as a starting material was recovered (45 mg, 39%).

EXAMPLE 4

{1-3-(4-Methoxycarbonyl-1-butenyl)-6-exo-t-butyldimethylsilyloxymethyl-7-endo-tetrahydropyranyloxybicyclo[3.3.0]oct-2-ene} (116 mg, 0.25 mmol) and mesitylenetricarbonyl molybdenum (15 mg, 0.05 mmol) were dissolved in acetone (10 ml) and then degassed. In a 100 ml of autoclave under 70 kg/cm$^2$ of hydrogen gas pressure, the reaction was carried out at 100°C. for 12 hours. Evaporation of the solvent followed by purification through silica gel column chromatography (ether:n-hexane=1:5) afforded {3E-(4-metnoxycarbonylbutylidene)-6-exo-t-butyldimethylsilyloxymethyl-7-endo-tetrahydropyranyloxybicyclo[3.3.0]octane} (60 mg, Yield: 52%). The spectrum data of the obtained product are completely agreed with those of the compound obtained in Example 1. From the results of the analysis by using a gas chromatography, the product did not contain a Z-isomer at all.

EXAMPLE 5

{1-3-(4-Methoxycarbonyl-1-butenyl)-6-exo-t-butyldimethylsilyloxymethyl-7-endo-tetrahydropyranyloxybicyclo[3.3.0]oct-2-ene} (116 mg, 0.25 mmol) and mesitylenetricarbonyl tungsten (18 mg, 0.05 mmol) were dissolved in acetone (10 ml) and then degassed. In a 100 ml of autoclave under 70 kg/cm$^2$ of hydrogen gas pressure, the reaction was carried out at 120° C. for 12 hours. Evaporation of the solvent followed by purification through silica gel column chromatograghy (ether:n-hexane=1:5) afforded {3E-(4-methoxycarbonylbutylidene)-6-exo-t-butyldimethylsilyloxymethyl-7-endo-tetrahydropyranyloxybicyclo[3.3.0]octane} (18 mg, Yield: 15%). The spectrum data of the obtained product are completely agreed with those of the compound obtained in Example 1. From the results of the analysis by using a gas chromatography, the product did not contain a Z-isomer at all.

EXAMPLE 6

{L-3-(4-Methoxycarbonyl-1-butenyl)-6-exo-t-butyldimethylsilyloxymethyl-7-endo-tetrahydropyranyloxybicyclo[3.3.0]oct-2-ene} (116 mg, 0.25 mxol) and triphenylphosphinepentacarbonyl chromium (18 mg, 0.05 mmol) were dissolved in acetone (10 ml) and degassed by a repetition of a cycle of cooling-diminished pressure-dissolution using liquid nitrogen. The resultant mixture was transferred into 100 ml of autoclave and 70 kg/cm$^2$ of hydrogen gas was charged therein. After completion of the reaction at 180° C. for 15 hours, the solvent was distilled out and then the residue was roughly purified through column chromatography (ether). The products which contain a detetrahydropyranylated compound caused by thermal reaction were combined and protected again with tetrahydropyranyl ether by using dihydropyran-para-toluene sulfonic acid in methylene chloride. Purification through silica gel column chromatography (ether : n-hexane=1:5) afforded {3E-(4-methoxycarbonylbutylidene)-6-exo-t-butyldimethylsilyloxymethyl-7-endo-tetrahydropyranyloxybicyclo[3.3.0]octane} (11 mg, Yield: 10%). The spectrum data thereof are completely agreed with those of the compound obtained in Example 1. The obtained product did not contain a Z-isomer at all from the result of the analysis by using a gas chromatography.

EXAMLE 7

{1-3-(4-Methoxycarbonyl-1-butenyl)-6-exo-t-butyldimethylsilyloxymethyl-7-endo-tetrahydropyranyloxybicyclo[3.3.0]oct-2-ene} (116 mg, 0.25 mmol) and hydridcyclopentadienyltricarbonyl chromium (10 mg, 0.05 mmol) were dissolved in acetone (10 ml) and then degassed by a repetition of a cycle of cooling-diminished pressure-dissolution using liquid nitrogen. The mixture was transferred in a 100 ml of autoclave and 90 kg/cm$^2$ of hydrogen gas was charged thereinto. After completion of the reaction at 100° C. for 15 hours, the solvent was distilled out and the residue was purified through silica gel column chromatography (ether:n-hexane=1:5) to obtain {3E-(4-methoxycarbonylbutylidene)-6-exo-t-butyldimethylsilyloxymethyl-7-endo-tetrahydropyranyloxybicyclo[3.3.0]octane} (66 mg, Yield: 56%). The spectrum data of the obtained product are completely agreed with those of the compound obtained in Example 1. From the results of the analysis by using a gas chromatography, the product did not contain a Z-isomer at all.

EXAMPLE 8

{1-3-(4-Methoxycarbonyl-1-butenyl)-6-exo-(1-methyl-1-mthoxyethyloxymethyl)-7-endo-tetrahydropyranyloxybicyclo[3.3.0]oct-2-ene} (106 mg, 0.25 mmol) and methylbenzoatetricarbonyl chromium (14 mg, 0.05 mmol) were dissolved in acetone (10 ml) and then degassed. In a 100 ml of autoclave under 70 kg/cm$^2$ of hydrogen gas pressure, the reaction was carried out at 120° C. for 15 hours. Evaporation of the solvent followed by purification through silica gel column chromatography (ether:n-hexane=1:4) afforded {3E-(4-methoxycarbonylbutylidene)-6-exo-(1-methyl-1-methoxyethyloxymethyl)-7-endo-tetrahydropyranyloxybicyclo[3.3.0]octane} (95 mg, Yield: 90%). The obtained product did not contain a Z-isomer at all with regard to a double bond from the results of the analysis by using a gas chromatography.

IR (neat): 2970, 2880, 1743, 835 cm$^{-1}$. NMR δ (CDCl$_3$): 5.20 (t, J=7 Hz, 1H), 4.65 (m, 1H), 3.70 (s, 3H), 3.30–4.10 (m, 5H), 3.20 (s, 3H), 1.33 (s, 6H).

Mass m/z (%): 424 (M+), 393, 340, 85, 73.

EXAMPLE 9

{1-3-(4-Methoxycarbonyl-1-butenyl)-6-exo-hydroxymethyl-7-endo-tetrahydropyranyloxybicyclo[3.3.0]oct-2-ene} (88 mg, 0.25 mmol) and methylbenzoatetricarbonyl chromium (14 mg, 0.05 mmol) were dissolved in acetone (10 ml) and then degassed. In a 100 ml of autoclave under 70 kg/cm$^2$ of hydrogen gas pressure, the reaction was carried out at 120° C. for 15 hours. Evaporation of the solvent followed by purification through silica gel column chromatography (ether:n-hexane=1:2) afforded {d-3E-(4-methoxycarbonylbutylidene)-6-exo-hydroxymethyl-7-endo-tetrahydropyranyloxybicyclo[3.3.0]octane} (78 mg, Yield: 89%) The obtained product did not contain a Z-isomer at all with regard to a double bond from the results of the analysis by using a gas chromatography.

IR (neat): 3480, 2950, 1741 cm$^{-1}$.

NMR δ (CDCl$_3$): 5.22 (t, J=7 Hz, 1H), 4.65 (m, 1H), 3.65 (m, 1H), 3.30–4.20 (m, 5H).

Mass m/z (%): 334 (2), 268 (19), 250 (15), 232 (38), 219 (22), 91 (26), 86 (33), 85 (100).

[α]$_D^{20}$=+6° (c=1.476, MeOH).

EXAMPLE 10

{1-3-(4-Methoxycarbonyl-1-butenyl)-6-exo-t-butyldimethylsilyloxymethyl-7-endo-(1-methyl-1-methoxyethyloxy)bicyclo[3.3.0]oct-2-ene} (113 mg, 0.25 mmol) and methylbenzoatetricarbonyl chromium (14 mg, 0.05 mmol) were dissolved in acetone (10 ml) and then degassed. In a 100 ml of autoclave under 70 kg/cm$^2$ of hydrogen gas pressure, the reaction was carried out at 120° C. for 15 hours. Evaporation of the solvent followed by purification through silica gel column chromatography (ether : n-hexane=1:4) afforded {3E-(4-methoxycarbonylbutylidene)-6-exo-t-butyldimethylsilyloxymethyl)-7-endo-(1-methyl-1-methoxyethyloxy)-bicyclo[3.3.0]octane} (102 mg, Yield: 90%). The obtained product did not contain a 5-Z isomer from the results of the analysis by using a gas chromatography.

IR (neat): 2970, 2880, 1743, 835 cm$^{-1}$.

NMR δ (CDCl$_3$): 5.21 (t, J=7 Hz, 1H), 3.70 (s, 3H), 3.30–4.10(m, 3H), 3.20 (s, 3H), 1.33 (s, 6H), 0.90 (s, 9H), 0.05 (s, 6H).

Mass m/z (%): 454, 422, 382, 73, 59.

EXAMPLE 11

{1-3-(4-Carboxy-1-butenyl)-6-exo-t-butyldimethylsilyloxymethyl-7-endo-tetrahydropyranyloxybicyclo[3.3.0]oct-2-ene} (113 mg, 0.25 mmol) and methylbenzoatetricarbonyl chromium (14 mg, 0.05 mmol) were dissolved in acetone (10 ml) and then degassed. In a 100 ml of autoclave under 70 kg/cm$^2$ of hydrogen gas pressure, the reaction was carried out at 120° C. for 15 hours. Evaporation of the solvent followed by purification through silica gel column chromatography (ether) afforded {3E-(4-carboxybutylidene)6-exo-t-butyldimethylsilyloxymethyl-7-endo-tetrahydropyranyloxybicyclo[3.3.0]octane} (62 mg, Yield: 55%). The obtained product was treated with diazomethane to obtain a methyl ester compound. The spectrum data of the compound are completely agreed with those of the compound obtained in Example 1. From the results of the analysis by using a gas chromatography, the methyl ester compound did not contain a 5-Z isomer at all.

REFERENCE EXAMPLE 12

In THF (1.5 ml) was dissolved (3E-(4-methoxycarbonylbutylidene)-6-exo-t-butyldimethylsilyloxymethyl-7-endotetrahydropyranyloxybicyclo[3.3.0]octane} (100 mg, 0.21 mmol). To the solution was added a solution of tetra-n-butylammonium fluoride (0.32 ml, 0.32 mmol) dissolved in 1 M of THF. After the mixture was stirred at room temperature for 13 hours, a saturated saline solution was added thereinto and THF was distilled off under reduced pressure. The resultant aqueous layer was extracted with ether and dried with anhydrous magnesium sulfate, and then the solvent was distilled off. The residue was purified through silica gel column chromatography (ether:n-hexane=3:2) to obtain (d-3E-(4-methoxycarbonylbutylidene)-6-exo-hydroxymethyl-7-endo-tetrahydropyranyloxybicyclo[3.3.0]octane} (74 mg, Yield: 98%). Various spectrum data thereof are completely agreed with those of the substance onbtained in Example 9.

REFERENCE EXAMPLE 13

In THF (2.4 ml) was dissolved {3E-(4-methoxycarbonylbutylidene)-6-exo-(1-methyl-1-methoxyethyloxymethyl)-7-endo-tetrahydropyranyloxybicyclo[3.3.0]octane} (95 mg, 0.22 mmol). To the solution was added a 0.5 N HCl (1.2 ml) under ice-cooling and the mixture was stirred for 10 minutes under the same condition. To the mixture was added ethyl acetate (24 ml) and the separated organic layer was washed with water and a saturated saline solution and then dried with anhydrous magnesium sulfate. After evaporation of the solvent, the residue was purified through silica gel column chromatography (ether:n-hexane=1:2) to obtain {d-3E-(4-methoxycarbonylbutylidene)-6-exo-hydroxymethyl-7-endo-tetrahydropyranyloxybicyclo[3.3.0]octane} (74 mg, Yield: 90%). Various spectrum data thereof are completely agreed with those of the substance obtained in Example 9.

REFERENCE EXAMPLE 14

Under argon gas atmosphere, in DMSO (1.5 ml) were dissolved {d-3E-(4-methoxycarbonylbutylidene)-6-exo-hydroxymethyl-7-endo-tetrahydropyranyloxybicyclo[3.3.0]octane} (49 mg, 0.14 mmol) and triethylamine (0.12 ml). To the mixture was added sulfur trioxide.-pyridine complex (67 mg, 0.42 mmol) in DMSO solution (1 ml) and the mixture was stirred at room temperature for an hour. The reaction mixture was poured into ice-cold water and then extracted with ether. The separated ether layer was washed with water and a saturated saline solution. After driness with anhydrous magnesium sulfate, evaporation of the solvent afforded {3E-(4-methoxycarbonylbutylidene)-6-exo-formyl-7-endo-tetrahydropyranyloxybicyclo[3.3.0]octane}.

On the other hand, sodium hydride (60% oily material, 8 mg, 0.2 mmol) was washed with pentane under argon gas atmosphere and then suspended in THF (1.4 ml). To the thus prepared mixture was added a THF solution (0.2 ml) of dimethyl(2-oxoheptyl)phosphonate (47 mg, 0.21 mmol), followed by stirring at room temperature for 30 minutes. To the resultant mixture was added the previously prepared THF solution (0.6 ml) of {3E-(4-methoxycarbonylbutylidene)-6-exo-formyl-7-endo-tetrahydropyranyloxybicyclo[3.3.0]octane}.

After the resultant mixture was stirred at room temperature for further 30 minutes, a saturated aqueous ammonium chloride solution was added thereto. The thus prepared mixture was extracted with ether and the separated ether layer was washed with a saturated saline solution. The resultant mixture was dried with anhydrous magnesium sulfate and the solvent was distilled off. The residue was purified through silica gel colomn chromatography (ether:n-hexane=2:5) to obtain {3-(4-methoxycarbonylbutylidene)-6-exo(3-oxo-trans-1-octenyl)-7-endo-tetrahydropyranyloxybicyclo[3.3.0]octane} (52 mg, Yield: 84%).

IR (neat): 2950, 1740, 1700, 1675, 1630 cm$^{-1}$.

nmr δ (CDCl$_3$): 6.75 (m, 1H), 6.17, 6.13 (2xd, J=16 Hz, 1H), 5.25 (t, J=7 Hz, 1H), 4.60 (m, 1H), 3.68 (s, 3H), 3.30–4.20 (m, 3H), 0.90 (t, J=6 Hz, 1H).

Mass m/z: 362 (5), 344 (7), 167 (13), 149 (41), 85 (34), 74 (23), 73 (25), 61 (34), 59 (31), 57 (31), 45 (100), 43 (77), 31 (78), 29 (51).

REFERENCE EXAMPLE 15

In THF (0.09 ml) was dissolved (3E-(4-methoxycarbonylbutylidene)-6-exo-(3-oxo-trans-1-octenyl)-7-endo-tetrahydropyranyloxybicyclo[3.3.0]octane} (50 mg, 0.11 mmol) and to the solution was added a 65% aqueous acetic acid solution (0.9 ml) at room temperature. After the mixture was stirred at 50° C. for 2 hours, the resultant mixture was poured into cooled saturated sodium hydrogencarbonate solution. The mixture was extracted with ether and the separated ether layer was washed with a saturated saline solution, dried with anhydrous magnesium sulfate and then the solvent was distilled off under reduced pressure. The obtained residue was purified through silica gel column chromatography (ether:n-hexane=3:2) to yield {d-3E-(4-methoxycarbonylbutylidene)-6-exo-(3-oxo-trans-1-octenyl)-7-endo-hydroxybicyclo[3.3.0]octane} (39 mg, Yield: 96%).

The spectrum data of NMR, IR and Mass of the resultant product were completely agreed with those described in the literature (Tetrahedron, Vol. 37, No. 25, pp. 4391–4399, 1981). Further, In the analysis of the product by using a TLC which employs ethyl acetate:-cyclohexane=1:2 as an eluent capable of separating an E-isomer and a Z-isomer from the product in accordance with the literature, it was confirmed that the product was a single compound.

IR (neat): 3430, 1740, 1695, 1670, 1625, 1435, 1375, 1320, 1250, 1170, 1135, 1080, 985 cm$^{-1}$. nmr δ (CDCl$_3$): 6.77 (dd, J=15.5 Hz, 8.0 Hz, 1H), 6.17 (d, J=15.5 Hz, 1H), 5.25 (m, 1H), 3.90 (m, 1H), 3.66 (s, 3H), 0.90 (m, 3H).

Mass m/z: 362, 344, 318, 313, 245, 179, 164, 147, 131, 129, 105.

Further, in the above literature, there is disclosed that the above product could be led to a carbacycline in high yield.

REFERENCE EXAMPLE 16

In THF (1 ml) was dissolved {3E-(4-methoxycarbonylbutylidene)-6-exo-t-butyldimethylsilyloxymethyl-7-endo-(1-methyl-1-methoxyethyloxy)-bicyclo[3.3.0]octane} (50 mg, 0.11 mmol). To the solution was added a solution of tetra-n-butylammonium fluoride (0.2 ml) dissolved in 1 M of THF and the mixture was stirred at room temperature for 13 hours. After the solvent was distilled off under reduced pressure, to the residue was added water and the mixture was extracted with ether. The separated ether layer was washed with a saturated saline solution and then dried with anhydrous magnesium sulfate. After evaporation of the solvent, the residue was purified through silica gel column chromatography (ether:n-hexane=1:1) to obtain (3E-(4-methoxycarbonylbutylidene)-6-exo-hydroxymethyl-7-endo-(1-methyl-1-methoxyethyloxy)-bicyclo[3.3.-0]octane} (35 mg, Yield: 95%) as a colorless oily product.

IR (neat): 3480, 2950, 1740 cm$^{-1}$. nmr δ (CDCl$_3$): 5.22 (t, J=7 Hz, 1H), 3.65 (s, 3H), 3.30–4.20 (m, 3H), 3.20 (s, 3H), 1.30 (s, 6H).

Mass m/z: 340, 322, 309, 268, 73.

REFERENCE EXAMPLE 17

The same procedures were carried out as in Reference example 14 except that (3E-(4-methoxycarbonylbutylidene)-6-exo-hydroxymethyl-7-endo-(1-methyl-1-methoxyethyloxy)bicyclo[3.3.0]octane} (35 mg, 0.10 mmol) was employed as a starting material to yield {3E-(4-methoxycarbonylbutylidene)-6-exo-(3-oxo-1-trans-octenyl)-7-endo-(1-methyl-1-methoxyethyloxy)-bicyclo[3.3.0]octane} (35 mg, Yield: 80%) as a nearly colorless oily product.

IR (neat): 2950, 1740, 1700, 1675, 1630 cm$^{-1}$. nmr δ (CDCl$_3$): 6.75 (m, 1H), 6.17, 6.12 (2xd, J=16 Hz, 1H), 5.25 (t, J=7 Hz, 1H), 3.90 (m, 1H), 3.68 (s, 3H), 3.20 (s, 3H), 1.34 (s, 6H), 0.90 (t, J=6 Hz, 1H).

Mass m/z (%): 434, 403, 362, 73.

REFERENCE EXAMPLE 18

The same procedures were carried out as in Reference example 15 except that (3E-(4-methoxycarbonylbutylidene)-6-exo-(3-oxo-1-trans-octenyl)-7-endo-(1-methyl-1-methoxyethyloxy)-bicyclo[3.3.0]octane} (35 mg, 0.081 mmol) was employed as a starting material to yield {d-3-E-(4-methoxycarbonylbutylidene)-6-exo-(3-oxo-1-trans-octenyl)-7-endo-hydroxybicyclo[3.3.0]octane} (26 mg, Yield: 90%). The spectrum data of the obtained product are completely agreed with those of the compound obtained in Reference example 15.

REFERENCE EXAMPLE 19

{1-3-(4'-Methoxycarbonyl-1'-butenyl)-6-exo-t-butyldimethylsilyloxymethyl-7-endo-tetrahydropyranyloxybicyclo[3.3.0]oct-2-ene} (464 mg, 1 mmol) was dissolved in THF (4.6 ml). To the thus prepared solution was added a tetra-n-butylammonium fluoride solution (1M THF solution, 1.5 ml), followed by stirring at room temperature for 13 hours. After the solvent was distilled out under reduced pressure, to the residue was added water, followed by extraction with ether. The separated ether layer was washed with a saturated saline solution, and dried with anhydrous magnesium sulfate. After the solvent was distilled off, the residue was purified through silica gel column chromatography (ether:n-hexane=1:2) to obtain (3-(4'-methoxycarbonyl-1'-butenyl)-6-exo-hydroxymethyl-7-endo-tetrahydropyranyloxybicyclo[3.3.0]oct-2-ene} (333 mg, Yield: 95%) as colorless oily product.

IR (neat): 3480, 1740 cm$^{-1}$.

nmr δ (CDCl$_3$): 6.26 (d, J=15 Hz, ⅖H, trans), 6.00 (d, J=12 Hz, ⅗H, cis), 5.58 (s, 1H), 5.35 (m, 1H), 4.62 (m, 1H), 3.68 (s, 3H), 3.30–4.30 (m, 5H), 3.00 (m, 1H).

Mass m/z: 350, 266.

REFERENCE EXAMPLE 20

{3-(4'-Carboxy-1'-butenyl)-6-exo-t-butyldimethylsilyloxymethyl-7-endo-tetrahydropyranyloxybicyclo[3.3.0]oct-2-ene} (450 mg, 1 mmol) was dissolved in acetonitrile (2 ml). To the thus prepared solution were added DBU (304 mg, 2 mmol) and ethyl iodide (468 mg, 3 mmol) at room temperature, followed by stirring for further 3 hours. After the reaction was stopped with addition of a saturated aqueous ammonium chloride solution, the resultant mixture was extracted with ether. The separated ether layer was washed with a saturated saline solution, followed by drying with anhydrous magnesium sulfate. After the solvent was distilled out, the residue was purified through silica gel column chromatography to obtain {3-(4'-ethoxycarbonyl-1'-butenyl)-6-exo-t-butyldimethylsilyloxymethyl-7-endo-tetrahydropyranyloxybicyclo[3.3.0]oct-2-ene (400 mg, Yield: 84%) as colorless oily product.

IR (neat); 2950, 2870, 1745, 840 cm$^{-1}$.

nmr δ (CDCl$_3$); 6.24 (d, J=16 Hz, ⅖H, trans), 5.98 (d, J=11Hz, ⅗H, cis), 5.57 (bs, 1H), 5.30 (m, 1H), 4.60 (bs, 1H), 4.20 (q, J=7 Hz, 2H), 3.20 - 4.20 (m, 5H), 2.95 (m, 1H), 1.30 (t, J=7 Hz, 3H), 0.90 (s, 9H).

Mass m/z; 478 (M$^+$), 433, 421, 393.

In THF (4 ml) was dissolved {3-(4'-ethoxycarbonyl-1'-butenyl)-6-exo-t-butyldimethylsilyloxymethyl-7-endo-tetrahydropyranyloxybicyclo[3.3.0]oct-2-ene} (400 mg, 0.84 mmol). To the thus prepared solution was added a tetra- butylammonium fluoride (1M THF solution, 1.3 ml), followed by stirring at room temperature for 12 hours. After the reaction was stopped by adding a saturated aqueous ammonium chloride solution, THF was distilled out under reduced pressure. The resultant aqueous layer was extracted with an ether and the separated ether layer was washed with a saturated saline solution, followed by drying with anhydrous magnesium sulfate. After the solvent was distilled off, the residue was purified through silica gel column chromatography to obtain {3-(4'-ethoxycarbonyl1'-butenyl)-6-exo-hydroxymethyl-7-endo-tetrahydropyranyloxybicyclo[3.3.0]oct-2-ene} (306 mg, Yield: 100%) as nearly colorless oily product.

IR (neat): 3480, 1740 cm$^{31\ 1}$.

nmr δ (CDCl$_3$): 6.26 (d, J=15 Hz, ⅖H, trans), 6.00 (d, J=12 Hz, ⅗H, cis), 5.58 (s, 1H), 5.32 (m, 1H), 4.60 (m, 1H), 3.30–4.30 (m, 5H), 4.20 (q, J=7 Hz, 2H), 3.00 (m, 1H), 1.30 (t, J=7 Hz, 3H).

Mass m/z: 364, 280.

REFERENCE EXAMPLE 21

Under argon gas atmosphere, {3-(4'-methoxycarbonyl-1'-butenyl)-6(S)-hydroxymethyl-7(R)-tetrahydropyranyloxy-(1S,5S)-cis-bicyclo[3.3.0]oct-2-ene} (stereochemistry of the double bond is E:Z=1:2) (422 mg, 1.2 mmol) and triethylamine (0.98 ml) were dissolved in DMSO (10 ml). To the thus prepared solution was added a DMSO solution (7.5 ml) of sulfurtrioxide-pyridine complex (575 mg, 3.6 mmol), followed by stirring at room temperature for 30 minutes. The resultant mixture was poured into the ice-cold water, followed by extraction with ether. The separated ether layer was washed with water and a saturated saline solution. The residue was dried with anhydrous magnesium sulfate and the solvent was distilled out to obtain {3-(4'-methoxycarbonyl-1'-butenyl)-6(R-formyl-7(R)-tetrahydropyranyloxy-(1S,5S)-cis-bicyclo[3.3.0]oct-2-ene}.

On the other hand, sodium hydride (60% oily material, 67 mg, 1.68 mmol) was washed with an n-pentane and suspended in THF (10 ml). To the thus prepared mixture was added a THF solution (3 ml) of dimethyl(2-oxo-3-methyl-5-heptynyl)phosphonate (418 mg, 1.8 mmol), followed by stirring at room temperature for 30 minutes. To the resultant mixture was added the above-mentioned THF solution (6 ml) of {3-(4'-methoxycarbonyl-1'-butenyl)-6(R)-formyl-7(R)-tetrahydropyranyloxy-(1S, 5S)-cis-bicyclo[3.3.0]oct-2-ene}. After the resultant mixture was stirred at room temperature for further 1 hour, a saturated aqueous ammonium chloride solution was added thereto. The thus prepared mixture was extracted with ether and the separated ether layer was washed with a saturated saline solution. The resultant mixture was dried with anhydrous magnesium sulfate and the solvent was distilled out. The residue was purified through silica gel colomn chromatography to obtain {3-(4'-methoxycarbonyl-1'-butenyl)-6(S)-(3'-oxo-4'(RS)-methyl-trans-1'-octen-6'-ynyl)-7(R)-tetrahydropyranyloxy-(1S5S)-cis-bicyclo[3.3.0]oct-2-ene} (460 mg, Yield: 84%) as colorless oily product.

IR (neat): 1740, 1695, 1680, 1625 cm$^{-1}$.

NMR δ (CDCl$_3$): 6.80 (m, 1H), 5.80–6.50 (m, 2H), 5.00–5.70 (m, 2H), 4.60 (m, 1H), 3.68 (s, 3H), 1.75 (t, J=2 Hz, 3H), 1.20 (d, J=7 Hz, 3H).

Mass m/z: 454, 370, 85.

REFERENCE EXAMPLE 22

The reaction was carried out following the same procedure as in Reference example 21 to synthesize {3-(4'-methoxycarbonyl-1'-butenyl)-6(R)-formyl-7(R)-tetrahydropyranyloxy-(1S, 5S)-cisbicyclo[3.3.0]oct-2-ene}. The thus obtained compound was reacted with dimethyl-(2-oxo-4(R)-methyl-8-methyl-7-nonenyl)-phosphonate (479 mg, 1.8 mmol) to obtain {3-(4'-methoxycarbonyl-1'-butenyl)-6(S)-(3'-oxo-5'(R)-methyl-9'-methyl-trans-1'-decen-8'-enyl)-7(R)-tetrahydropyranyloxy-(1S,5S)-cis-bicyclo[3.3.0]oct-2-ene} (500 mg, Yield: 85%).

IR (neat): 1745, 1700, 1675, 1625 cm$^{-1}$.

NMR δ (CDCl$_3$): 6.80 (m, 1H), 5.80–6.50 (m, 2H), 4.90–5.70 (m, 3H), 4.65 (m, 1H), 3.70 (s, 3H), 0.93 (d, J=6 Hz, 3H).

Mass m/z: 414, 396, 85.

REFERENCE EXAMPLE 23

The reaction was carried out following the same procedures as in Reference example 21 except for using {3-(4'-ethoxycarbonyl-1'-butenyl)-6(S)-hydroxymethyl-7(R)-tetrahydropyranyloxy-(1S, 5S)-cis-bicyclo[3.3.0]oct-2-ene} (437 mg, 1.2 mmol) to synthesize {3-(4'-ethoxycarbonyl-1'-butenyl)-6(R)-formyl-7(R)-tetrahydropyranyloxy-(1S,5S)-cis-bicyclo[3.3.0]oct-2-ene} and finally yielded {3-(4'-ethoxycarbonyl-1'-butenyl)-6(S)-(3'-oxo-5'(R)-methyl-trans-1'-decen-8'-enyl)-7(R)-tetrahydropyranyloxy-(1S,5S)-cis-bicyclo[3.3.0]oct-2-ene} (522 mg, Yield: 85%) as colorless oily product.

IR (neat): 1745, 1695, 1680, 1625 cm$^{-1}$.

NMR δ (CDCl$_3$): 6.80 (m, 1H), 5.80–6.50 (m, 2H), 4.90–5.70 (m, 3H), 4.65 (m, 1H), 4.20 (q, 2H, J=7 Hz), 1.30 (t, J=7 Hz, 3H), 0.93 (d, J=6 Hz, 3H).

Mass m/z: 428, 410.

REFERENCE EXAMPLE 24

The reaction was carried out following the same procedures as in Reference example 21 except for using {3-(4'-methoxycarbonyl-1'-butenyl)-6(S)-hydroxymethyl-7(R)-tetrahydropyranyloxy-(1S, 5S)-cis-bicyclo[3.3.0]oct-2-ene} (422 mg, 1.2 mmol) to synthesize {3-(4'-methoxycarbonyl-1'-butenyl)-6(R)-formyl-7(R)-tetrahydropyranyloxy-(1S,5S)-cis-bicyclo[3.3.0]oct-2-ene} and finally yielded {3-(4'-methoxycarbonyl-1'-butenyl)-6(S)-(3'-oxo-trans-1'-octenyl)-7(R)-tetrahydropyranyloxy-(1S,5S)-cis-bicyclo[3.3.0]oct-2-ene} (458 mg, Yield: 86%) as colorless oily product.

IR (neat): 1740, 1680, 1625 cm$^{-1}$.

NMR δ (1DCl$_3$): 6.75 (m, 1H), 5.80–6.40 (2H), 5.00–5.70 (m, 2H), 4.60 (m, 1H), 3.67 (s, 3H).

Mass m/z: 444, 360.

REFERENCE EXAMPLE 25

The reaction was carried out following the same procedures as in Reference example 21 except for using {3-(4'-methoxycarbonyl-1'-butenyl)-6(S)-hydroxymethyl-7(R)-tetrahydropyranyloxy-(1S,5S)-cis-bicyclo[3.3.0]oct-2-ene} (422 mg, 1.2 mmol) to synthesize (3-(4'-methoxycarbonyl-1'-butenyl)-6(R)-formyl-7(R)-tetrahydropyranyloxy-(1S,5S)-cis-bicyclo[3.3.0]oct-2-ene} and finally yielded {3-(4'-methoxycarbonyl-1'-butenyl)-6(S)-(3'-oxo-3'-cyclopentyl-trans-1'-propenyl)-7(R)-tetrahydropyranyloxy-(1S,5S)-cis-bicyclo[3.3.0]oct-2-ene} (440 mg, Yield: 83%) as colorless oily product.

IR (neat): 1740, 1700, 1670, 1630 cm$^{-1}$.

NMR δ (CDCl$_3$): 6.80 (m, 1H), 5.80–6.50 (m, 2H), 5.00–5.70 (m, 2H), 4.60 (m, 1H), 3.68 (s, 3H).

Mass m/z: 442, 411, 358

REFERENCE EXAMPLE 26

The reaction was carried out following the same procedures as in Reference example 21 except for using {3-(4'-ethoxycarbonyl-1'-butenyl)-6(S)-hydroxymethyl-7(R)-tetrahydropyranyloxy-(1S, 5S)-cis-bicyclo[3.3.0]oct-2-ene} (437 mg, 1.2 mmol) to synthesize {3-(4'-ethoxycarbonyl-1'-butenyl)-6(R)-formyl-7(R)-tetrahydropyranyloxy-(1S,5S)-cis-bicyclo[3.3.0]oct-2-ene} and finally yielded {3-(4'-ethoxycarbonyl-1'-butenyl)-6(S)-(3'-oxo-4'(RS)-methyl-trans-1'-octen-6'-ynyl)-7(R)-tetrahydropyranyloxy-(1S,5S)-cis-bicyclo[3.3.0]oct-2-ene} (455 mg, Yield: 81%) as colorless oily product.

IR (neat): 1740, 1694, 1678, 1625 cm$^{-1}$.

NMR δ (CDCl$_3$): 6.80 (m, 1H), 5.80–6.50 (m, 2H), 5.00–5.70 (m, 2H), 4.60 (m, 1H), 4.20 (q, J=7 Hz, 2H), 1.75 (t, J=2 Hz, 3H), 1.30 (t, J=7 Hz, 3H), 1.20 (d, J=7 Hz, 3H).

Mass m/z: 468, 384.

REFERENCE EXAMPLE 27

The reaction was carried out following the same procedures as in Reference example 21 except for using {3-(4'-ethoxycarbonyl-1'-butenyl)-6(S)-hydroxymethyl-7(R)-tetrahydropyranyloxy-(1S,5S)-cis-bicyclo[3.3.0]oct-2-ene} (437 mg, 1.2 mmol) to synthesize {3-(4'-ethoxycarbonyl-1'-butenyl)-6(R)-formyl-7(R)-tetrahydropyranyloxy-(1S,5S)-cis-bicyclo[3.3.0]oct-2-ene} and finally yielded {3-(4'-ethoxycarbonyl-1'-butenyl)-6(S)-(3'-oxo-3'-cyclopentyl-trans-1'-propenyl)-7(R)-tetrahydropyranyloxy-(1S,5S)-cis-bicyclo[3.3.0]oct-2-ene} (454 mg, Yield: 83%) as colorless oily product.

IR (neat): 1740, 1700, 1670, 1630 cm$^{-1}$.

NMR δ (CDCl$_3$): 6.80 (m, 1H), 5.80–6.50 (m, 2H), 5.00–5.70 (m, 2H), 4.60 (m, 1H), 4.20 (q, J=7 Hz, 2H), 1.30 (t, J=7 Hz, 3H).

Mass m/z: 456, 372.

REFERENCE EXAMPLE 28

In methanol (2.6 ml) was dissolved {3-{4'-Methoxycarbonyl-1'-butenyl)-6(S)-(3'-oxo-trans-1'-octenyl)-7(R)-tetrahydropyranyloxy-(1S,5S)-cis-bicyclo[3.3.0]oct-2-ene} (73 mg, 0.16 mmol). With addition of sodium borohydride (6 mg, 0.16 mmol) at −25° C., the mixture was stirred at −25° C. for 40 minutes. After the reaction was stopped with addition of an acetone, a saturated aqueous ammonium chloride solution was added to the mixture. After the methanol was distilled out, the resultant aqueous layer was extraced with ether. The separated ether layer was washed with a saturated saline solution and dried with anhydrous magnesium sulfate. The solvent was distilled off and the residue was purified through silica gel column chromatography to obtain {3-(4'-methoxycarbonyl-1'-butenyl)-6(S)-(3'(RS)-hydroxy-trans-1'-octenyl)-7(R)-tetrahydropyranyloxy-(1S,5S)-cis-bicyclo[3.3.0]oct-2-ene} (74 mg, Yield: 100%) as nearly colorless oily product.

IR (neat): 3470, 1745 cm$^{-1}$.

NMR $\delta$ (CDCl$_3$): 6.28 (d, J=16 Hz, ⅔H, trans), 6.00 (d, J=11Hz, ⅓H, cis), 5.10–5.75 (m, 4H), 4.67 (m, 1H), 3.70 (s, 3H).

Mass m/z: 446, 230.

REFERENCE EXAMPLE 29

The reaction was carried out following the same procedures as in Reference example 28 except for using {3-(4'-methoxycarbonyl-1'-butenyl)-6(S)-(3'-oxo-3'-cyclopentyl-trans-1'-propenyl)-7(R)-tetrahydropyranyloxy-(1S,5S)-cis-bicyclo[3.3.0]oct-2-ene} (130 mg, 0.29 mmol) to obtain {3-(4'-methoxycarbonyl-1'-butenyl)-6(S)-(3'(RS)-hydroxy-3'-cyclopentyl-trans-1'-propenyl)-7(R)-tetrahydropyranyloxy-(1S, 5S)-cis-bicyclo[3.3.0]oct-2-ene} (131 mg, Yield: 100%) as colorless oily product.

IR (neat): 3500, 1742 cm$^{-1}$.

nmr $\delta$ (CDCl$_3$): 6.28 (d, J=16 Hz, ⅔H, trans), 6.00 (d, J=11Hz, ⅓H, cis), 5.10–5.80 (m, 4H), 4.70 (m, 1H), 3.70 (s, 3H).

Mass m/z: 444, 342, 298, 220.

REFERECE EXAMPLE 30

{3-(4'-Methoxycarbonyl-1'-butenyl)-6(S)-(3'-oxo-4'(RS)-methyl-trans-1'-octen-6'-ynyl)-7(R)-tetrahydropyranyloxy-(1S,5S)-cis-bicyclo[3.3.0]oct-2-ene} (450 mg, 0.99 mmol) was dissolved in methanol (10 ml). With addition of excess amount of sodium borohydride at −25° C., the mixture was stirred at −25° C. for 1 hour. After the reaction was stopped with addition of an acetone, a saturated aqueous ammonium chloride solution was added to the mixture. After the methanol was distilled out, the resultant aqueous layer was extraced with ether. The separated ether layer was washed with a saturated saline solution and dried with anhydrous magnesium sulfate. The solvent was distilled out and the residue was purified through silica gel column chromatography to obtain {3-(4'-methoxycarbonyl-1'-butenyl)-6(S)-(3'(RS)-hydroxy-4'(RS)-methyl-trans-1'-octen-6'-ynyl)-7(R)-tetrahydropyranyloxy-(1S,5S)-cis-bicyclo[3.3.0]oct-2-ene} (377 mg, Yield: 84%) as nearly colorless oily product.

IR (neat): 3500, 1745 cm$^{-1}$.

NMR $\delta$ (CDCl$_3$): 6.30, 6.02 (each d, J=16 Hz, J=12 Hz, 1H), 5.20–5.80 (m, 4H), 4.60 (m, 1H), 3.71 (s, 3H), 1.69 (t, J=2 Hz, 3H), 1.00 (m, 3H).

Mass m/z: 372, 354, 85.

REFERENCE EXAMPLE 31

The reaction was carried out following the same procedures as in Reference example 30 except for using {3-(4'-methoxycarbonyl-1'-butenyl)-6(S)-(3'-oxo-5'(R)-methyl-9'-methyl-trans-1'-decen-8'-enyl)-7(R)-tetrahydropyranyloxy-(1S,5S)-cis-bicyclo[3.3.0]oct-2-ene} (490 mg, 0.98 mmol) to obtain {3-(4'-methoxycarbonyl-1'-butenyl)-6(S)-(3'(RS)-hydroxy-5'(R)-methyl-9'-methyl-trans-1'-decen-8'-enyl)-7(R)-tetrahydropyranyloxy-(1S,5S)-cis-bicyclo[3.3.0]oct-2-ene} (492 mg, Yield: 100%) as nearly colorless oily product.

IR (neat): 3500, 1745 cm$^{-1}$.

NMR $\delta$ (CDCl$_3$): 6.26, 6.00 (each d, J=15 Hz, J=11Hz, 1H), 5.00–5.62 (m, 5H), 4.68 (m, 1H), 3.69 (s, 3H), 1.68 (s, 3H), 1.58 (s, 3H), 0.90 (d, J=6 Hz, 3H).

Mass m/z: 500, 482, 416, 85.

REFERENCE EXAMPLE 32

The reaction was carried out following the same procedures as in Reference example 28 except for using {3-(4'-ethoxycarbonyl-1'-butenyl)-6(S)-(3'-oxo-3'-cyclopentyl-trans-1'-propenyl)-7(R)-tetrahydropyranyloxy-(1S,5S)-cis-bicyclo[3.3.0]oct-2-ene} (132 mg, 0.29 mmol) to obtain {3-4'-ethoxycarbonyl-1'-butenyl)-6(S)-(3'(RS)-hydroxy-3'-cyclopentyl-trans-1'-propenyl)-7(R)-tetrahydropyranyloxy-(1S,5S)-cis-bicyclo[3.3.0]oct-2-ene) (133 mg, Yield: 100%) as nearly colorless oily product.

IR (neat): 3500, 1742 cm$^{-1}$.

NMR $\delta$ (CDCl$_3$): 6.28 (d, J=16 Hz, ⅔H, trans), 6.00 (d, J=11Hz, ⅓H, cis), 5.10–5.80 (m, 4H), 4.70 (m, 1H), 4.20 (q, J=7 Hz, 2H), 1.30 (t, J=7 Hz, 3H).

Mass m/z: 458, 356.

REFERENCE EXAMPLE 33

The reaction was carried out following the same procedures as in Reference example 28 except for using {3-(4'-ethoxycarbonyl-1'-butenyl)-6(S)-(3'-oxo-4'(RS)-methyl-trans-1'-octen-6'-ynyl)-7(R)-tetrahydropyranyloxy-(1S,5S)-cis-bicyclo[3.3.0]oct-2-ene} (136 mg, 0.29 mmol) to obtain {3-(4'-ethoxycarbonyl-1'-butenyl)-6(S)-(3'(RS)-hydroxy-4'(RS)-methyl-trans-1'-octen-6'-ynyl)-7(R)-tetrahydropyranyloxy-(1S,5S)-cis-bicyclo[3.3.0]oct-2-ene} (136 mg, Yield: 100%) as nearly colorless oily product.

IR (neat): 3500, 1743 cm$^{-1}$.

NMR $\delta$ (CDCl$_3$): 6.28 (d, J=16 Hz, ⅔H, trans), 6.00 (d, J=11Hz, ⅓H, cis), 5.10–5.80 (m, 4H), 4.70 (m, 1H), 4.20 (q, J=7 Hz, 2H), 1.75 (t, J=2 Hz, 3H), 1.30 (t, J=7 Hz, 3H), 1.20 (d, J=7 Hz, 3H).

Mass m/z: 470, 368.

REFERENCE EXAMPLE 34

The reaction was carried out following the same procedures as in Reference example 30 except for using {3-(4' ethoxycarbonyl-1'-butenyl)-6(S)-(3'-oxo-5'(R)-methyl-9'-methyl-trans-1'-decen-8'-enyl)-7(R)-tetrahydropyranyloxy-(1S,5S)-cis-bicyclo[3.3.0]oct-2-ene} (502 mg, 0.98 mxol) to obtain {3-(4'-ethoxycarbonyl-1'-butenyl)-6(S)-(3'(RS)-hydroxy-5'(R)-methyl-trans-1'-decen-6'-enyl)-7(R)-tetrahydropyranyloxy-(1S,5S)-cis-bicyclo[3.3.0]oct-2-ene} (504 mg, Yield: 100%) as nearly colorless oily product.

IR (neat): 3500, 1745 cm$^{-1}$.

NMR $\delta$ (CDCl$_3$): 6.26, 6.00 (each d, J=15 Hz, J=11Hz, 1H), 5.00–5.62 (m, 5H), 4.68 (m, 1H), 4.20 (q, J=7 Hz, 2H), 1.30 (t, J=7 Hz, 3H), 0.93 (d, J=6 Hz, 3H).

Mass m/z: 514, 496, 430.

REFERENCE EXAMPLE 35

In THF (0.16 ml) was dissolved {3-(4'-methoxycarbonyl-1'butenyl)-6(S)-(3'(RS)-hydroxy-trans-1'-octenyl)-7(R)tetrahydropyranyloxy-(1S,5S)-cis-bicyclo[3.3.0]oct-2-ene} (446 mg, 1 mmol). With addition of a 65% aqueous acetic acid solution (2.6 ml) thereto, the mixture was stirred at 50° C. for 2 hours. The resultant mixture was poured into a cooled saturated aqueous sodium hydrogencarbonate solution and the mixture was extracted with ethyl acetate. The separated organic layer was washed with a saturated saline solution and dried with anhydrous magnesium sulfate. The solvent was distilled off and the residue was purified through silica gel column chromatography to obtain (3-(4'-methoxycarbonyl-1'-butenyl)-6(S)-(3'(R)-hydroxy-trans-1'-octenyl)-7(R)-hydroxy-(1S,5S)-cis-bicyclo[3.3.-0]oct-2-ene} (119 mg, Yield: 33%) as a lower polarity component and {3-(4'-methoxycarbonyl-1'-butenyl)-6(S)-(3'(S)-hydroxy-trans-1'-octenyl)-7(R)-hydroxy-(1S,5S)-cis-bicyclo[3.3.0]oct-2-ene} (214 mg, Yield: 59%) as a higher polarity component, each as colorless oily products.

Spectrum data of the higher polarity component were as follows:

IR (neat): 3400, 1742 cm$^{-1}$.

NMR δ (CDCl$_3$): 6.30 (d, J=15 Hz, ½H, trans), 6.02 (d, J=11Hz, ⅔H, cis), 5.00–5.70 (m, 4H), 4.10 (m, 1H), 3.70 (s, 3H), 3.02 (m, 1H).

Mass m/z: 362, 344.

$[\alpha]_D^{20} = -35°$ (c=0.466, MeOH)

The spectrum data of the lower polarity component accorded with those of the higher polarity component.

REFERENCE EXAMPLE 36

The reaction was carried out following the same procedures as in Reference example 35 except for using {3-(4'-methoxycarbonyl-1'-butenyl)-6(S)-(3'(RS)-hydroxy-3'-cyclopentyl-trans-1'-propenyl)-7(R)-tetrahydropyranyloxy-(1S,5S)-cis-bicyclo[3.3.0]oct-2-ene} (444 mg, 1 mmol) to obtain, as a lower polarity component, {3-(4'-methoxycarbonyl-1'-butenyl)-6(S)-(3'(R)-hydroxy-3'-cyclopentyl-trans-1'-propenyl)-7(R)-hydroxy-(1S,5S)-cis-bicyclo[3.3.0]oct-2-ene} (94 mg, Yield: 26%) and, as a higher polarity component, {3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (198 mg, Yield: 55%), as colorless oily product, respectively.

The spectrum data of the higher polarity component were as follows:

IR (neat): 3400, 1740 cm$^{-1}$.

NMR δ (CDCl$_3$): 6.22 (d, J=15 Hz, ½H, trans), 5.95 (d, J=11Hz, ⅔H, cis), 5.17–5.75 (m, 4H), 3.65 (s, 3H), 3.40–4.00 (m, 2H).

Mass m/z: 360, 342.

$[\alpha]_D^{20} = -30°$ (c=1.16, MeOH)

The spectrum data of the lower polarity component accorded with those of the higher polarity component.

REFERENCE EXAMPLE 37

In THF (0.6 ml) was dissolved {3-(4'-methoxycarbonyl-1'-butenyl)-6(S)-(3'(RS)-hydroxy-4'(RS)-methyl-trans-1'-octen-6'-ynyl)-7(R)-tetrahydropyranyloxy-(1S,5S)-cis-bicyclo[3.3.0]oct-2-ene} (350 mg, 0.77 mmol). With addition of a 65% aqueous acetic acid solution (6 ml), the mixture was stirred at 50° C. for 2 hours. The resultant mixture was poured into a cooled saturated aqueous sodium hydrogencarbonate solution and the mixture was extracted with ethyl acetic acid ester. The organic layer was washed with a saturated saline solution and dried over anhydrous magnesium sulfate. The solvent was distilled out and the residue was purified through silica gel column chromatography to obtain, as a low polarity component, {3-(4'-methoxycarbonyl-1'-butenyl)-6(S)-(3'(R)-hydroxy-4'(RS)-methyl-trans-1'-octen-6'-ynyl)-7(R)-hydroxy-(1S,5S)-cis-bicyclo[3.3.0]oct-2-ene} (67 mg, Yield: 23%) and, as a high polarity component, {3-(4'-methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.-0]oct-2-ene} (143 mg, Yield: 50%), as colorless oily products, respectively.

Spectrum data of the higher polarity component were as follows:

IR (neat): 3400, 1740 cm$^{-1}$.

NMR δ (CDCl$_3$): 6.25, 6.00 (each d, J=16 Hz, J=12 Hz, 1H) 5.00–5.70 (m, 3H), 3.68 (s, 3H), 1.78 (t, J=2 Hz, 3H), 0.98 (m, 3H).

Mass m/z: 372, 354, 336.

$[\alpha]_D^{20} = -16°$ (c=1.86, MeOH)

The spectrum data of the lower polarity component accorded with those of the higher polarity component.

REFERENCE EXAMPLE 38

The reaction was carried out following the same procedures as in Reference example 37 except for using {3-(4'-methoxycarbonyl-1'-butenyl)-6(S)-(3'(RS)-hydroxy-5'(R)-methyl-9'-methyl-trans-1'-decene-8'-enyl)-7(R)-tetrahydropyranyloxy-(1S,5S)-cis-bicyclo[3.3.0]oct-2-ene} (350 mg, 0.70 mmol) to obtain, as a lower polarity component, {3-(4'-methoxycarbonyl-1'-butenyl)-6(S)-(3'(R)-hydroxy-5'(R)-methyl-9'-methyl-trans-1'-decene-8'-enyl)-7(R)-hydroxy-(1S,5S)-cis-bicyclo[3.3.0]oct-2-ene} (99 mg, Yield: 34%) and, as a higher polarity component, {3-(4'-methoxycarbonyl-1'-butenyl)-6(S)-(3'(S)-hydroxy-5'(R)-methyl-9'-methyl-trans-1'-decene-8'-enyl)-7(R)-hydroxy-(1S,5S)-cis-bicyclo[3.3.0]oct-2-ene} (126 mg, Yield: 43%), as nearly colorless oily product, respectively.

The spectrum data of the higher polarity component were as follows:

IR (neat): 3400, 1740 cm$^{-1}$.

NMR δ (CDCl$_3$): 6.25, 6.00 (each d, J=15 Hz, J=12 Hz, 1H), 5.10–5.80 (m, 5H), 3.70 (s, 3H), 1.70 (s, 3H), 1.62 (s, 3H), 0.95 (d, J=6 Hz, 3H).

Mass m/z: 416, 398, 380.

$[\delta]_D^{20} = -31°$ (c=2.29, MeOH)

The spectrum data of the lower polarity component accorded with those of the higher polarity component.

REFERENCE EXAMPLE 39

The reaction was carried out following the same procedures as in Reference example 35 except for using {3-(4'-ethoxycarbonyl-1'-butenyl)-6(S)-(3'(RS)-hydroxy-3'-cyclopentyl-trans-1'-propenyl)-7(R)-tetrahydropyranyloxy-1S,5S)-cis-bicyclo[3.3.0]oct-2-ene} (458 mg, 1 mmol) to obtain, as a lower polarity component, {3-(4'-ethoxycarbonyl-1'-butenyl)-6(S)-(3'(R)-hydroxy-3'-cyclopentyl-trans-1'-propenyl)-7(R)-hydroxy-(1S,5S)-cis-bicyclo[3.3.0]oct-2-ene} (75 mg, Yield: 20%) and, as a higher polarity component, {3-(4'-ethoxycarbonyl-1'-butenyl)-6(S)-(3'(S)-hydroxy-3'- cyclopentyl-trans-1'-propenyl)-7(R)-hydroxy-(1S,5S)-cis-bicyclo[3.3.0]oct-2-ene} (199 mg, Yield: 53%), as colorless and viscous oily products, respectively.

The spectrum data of the higher polarity component were as follows:

IR (neat): 3400, 1740 cm$^{-1}$.

NMR δ (CDCl$_3$): 6.22 (d, J=15 Hz, ⅓H, trans), 5.95 (d, J=11Hz, ⅔H, cis), 5.17–5.75 (m, 4H), 4.20 (q, J=7 Hz, 2H), 3.40–4.00 (m, 2H), 1.30 (t, J=7 Hz, 3H).

Mass m/z: 374, 356.

The spectrum data of the lower polarity component accorded with those of the higher polarity component.

REFERENCE EXAMPLE 40

The reaction was carried out following the same procedures as in Reference example 35 except for using {3-(4'-ethoxycarbonyl- 1'-butenyl)-6(S)-(3'(RS)-hydroxy-4'(RS)-methyl-trans-1'-octen-6'-ynyl)-7(R)-tetrahydropyranyloxy-(1S,5S)-cis-bicyclo[3.3.0]oct-2-ene} (470 mg, 1 mmol) to obtain, as a lower polarity component, }3-(4'-ethoxycarbonyl-1'-butenyl)-6(S)-(3'(R)-hydroxy-4'(RS)-methyl-trans-1'-octen-6'-ynyl)-7(R)-hydroxy-(1S,5S)-cis-bicyclo[3.3.0]oct-2-ene} (81 mg, Yield: 21%) and, as a higher polarity component, {3-(4'-ethoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (201 mg, Yield: 52%), as colorless oily products, respectively.

The spectrum data of the higher polarity component were as follows:

IR (neat): 3400, 1740 cm$^{-1}$.

NMR δ (CDCl$_3$): 6.22 (d, J=15 Hz, ⅓H, trans), 5.95 (d, J=11Hz, ⅔H, cis), 5.17–5.75 (m, 4H), 4.20 (q, J=7 Hz, 2H), 3.40–4.00 (m, 2H), 1.75 (t, J=2 Hz, 3H), 1.30 (t, J=7 Hz, 3H), 1.20 (d, J=7 Hz, 3H).

Mass m/z: 386, 368.

The spectrum data of the lower polarity component accorded with those of the higher polarity component.

REFERENCE EXAMPLE 41

The reaction was carried out following the same procedures as in Reference example 37 except for using {3-(4'-ethoxycarbonyl-1'butenyl )-6(S)-(3'(RS)-hydroxy-5'(R)-methyl-9'-methyl-trans-1'-decen-8'-enyl)-7(R)-tetrahydropyranyloxy-(1S,5S)-cis-bicyclo[3.3.0]oct-2-ene} (504 mg, 0.98 mmol) to obtain, as a lower polarity component, {3-(4'-ethoxycarbonyl-1'-butenyl)-6(S)-(3'(R)-hydroxy5'(R)-methyl-9'-methyl-trans-1'-decen-8'-enyl)-7(R)-hydroxy-(1S,5S)-cis-bicyclo[3.3.0]oct-2-ene} (139 mg, Yield: 33%) and, as a higher polarity component, {3-(4'-ethoxycarbonyl-1'-butenyl)-6(S)-(3'(S)-hydroxy-5'(R)-methyl-9'-methyl-trans-1'-decen-8'-enyl)-7(R)-hydroxy-(1S,5S)-cis-bicyclo[3.3.0]oct-2-ene} (194 mg, Yield: 46%), as colorless oily products, respectively.

The spectrum data of the higher polarity component were as follows:

IR (neat): 3400, 1740 cm$^{-1}$.

NMR δ (CDCl$_3$): 6.25, 6.00 (each d, J=15 Hz, J=12 Hz, 1H), 5.10–5.80 (m, 5H), 4.20 (q, J=7 Hz, 2H), 1.70 (s, 3H), 1.62 (s, 3H), 1.30 (t, J=7 Hz, 3H), 0.95 (d, J=7 Hz, 3H).

Mass m/z: 430, 412, 394.

The spectrum data of the lower polarity component accorded with those of the higher polarity component.

REFERENCE EXAMPLE 42

{3-(4'-Methoxycarbony-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (54 mg, 0.145 mmol) was dissolved in methanol (1.16 ml). A 10% aqueous sodium hydroxide solution (1.16 ml) was added to the thus prepared mixture at 0° C., followed by stirring at 0° C. for 8 hours. The reaction mixture was diluted with ether, followed by neutrization with a 10% aqueous hydrochloric acid solution under ice-cooling. Then, methanol was distilled out under reduced pressure. The resultant aqueous layer was adjusted to pH 3 to 4 and extracted with ethyl acetate. After the separated ether layer was dried with anhydrous magensium sulfate, the solvent was distilled out to obtain {3-(4'-carboxy-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct- 2-ene} (50 mg, Yield: 96%).

IR (neat): 3350, 2950, 1715 cm$^{-1}$.

NMR δ (CDCl$_3$): 6.32 (d, J=16 Hz, ⅓H, trans), 6.04 (d, J=11Hz, ⅔H, cis), 5.20–5.90 (m, 4H), 1.81(t, J=2 Hz, 3H), 1.00 (m, 3H).

REFERENCE EXAMPLE 43

{3-(4'-Methoxycarbonyl-1'-butenyl)-6(S)-(3'(S)-hydroxy-5'(R)-methyl-9'-methyl-trans-1'decen-8'-enyl)-7(R)-hydroxy-(1S,5S)-cis-bicyclo[3.3.0]octene} (40 mg, 0.086 mmol) was dissolved in methanol (0.69 ml). A 10% aqueous sodium hydroxide solution (1.16 ml) was added to the thus prepared solution at 0° C., followed by stirring at 0° C. for 8 hours. The resultant mixture was diluted with ether, and neutralized with a 10% aqueous hydrochloric acid solution under ice-cooling. After methanol was distilled out under reduced pressure, the resultant aqueous layer was adjusted to pH 3 to 4 and extracted with ethyl acetate. The separated organic layer was dried with anhydrous magnesium sulfate and the solvent was distilled out to obtain {3-(4'-carboxy-1'-butenyl)-6(S)-(3'(S)-hydroxy-5'(R)-methyl-9'-methyl-trans-1'-decen-8'-enyl)-7(R)-hydroxy-(1S,5S)-cis-bicyclo[3.3.0]-oct-2-ene} (37 mg, Yield: 95%).

IR (neat): 3350, 2950, 1715 cm$^{-1}$.

NMR δ (CDCl$_3$) 6.30 (d, J=16 Hz, ⅓H, trans) 6.02 (d, J=11Hz, ⅔H, cis), 5.28–5.75 (m, 4H), 5.12 (t, J=7 Hz, 1H), 1.61 (s, 3H), 1.68 (s, 3H), 0.93 (d, J=6 Hz, 3H).

REFERENCE EXAMPLE 44

{3-(4'-Methoxycarbonyl-1'-butenyl)-6(S)-(3'(S)-hydroxy-trans-1'-octenyl)-7(R)-hydroxy-(1S,5S)-cis-bicyclo[ 3.3.0]oct-2-ene} (362 mg, 1 mmol) was dissolved in DMF (1.5 ml). With addition of imidazole (204 mg, 3 mmol) and t-butyldimethylsilyl chloride (452 mg, 3 mmol), the resultant mixture was stirred at room temperature for 10 hours. The reaction was stopped by adding a saturated aqueous ammonium chloride solution and the mixture was extracted with ether. The separated ether layer was washed with a saturated saline solution and dried with anhydrous magnesium sulfate. The solvent was distilled out and the residue was purified through silica gel column chromatography to obtain {3-(4'-methoxycarbonyl1'-butenyl)-6(S)-(3'(S)-t-butyldimethylsilyloxy-trans-1'-octenyl)-7(R)-t-butyldimethylsilyloxy-(1S,5S)-cis-bicyclo[3.3.0]oct-2-ene} (590 mg, Yield: 100%) as nearly colorless oily product.

IR (neat): 1750, 840 cm$^{-1}$.

NMR δ (CDCl₃): 6.27 (d, J=16 Hz, ½H, trans), 6.02 (d, J=11Hz, ⅜H, cis), 5.51 (m, 4H), 4.07 (m, 1H), 3.70 (m, 1H), 3.69 (s, 3H).
Mass m/z: 590, 534, 533, 519.
[α]$_D^{20}$=−37° (c=0.61, CHCl₃).

REFERENCE EXAMPLE 45

The reaction was carried out following the same procedures as in Reference example 44 except for using {3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (360 mg, 1 mmol) to obtain {3-(4'-methoxycarbonyl-1'-butenyl)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]oct-2-ene} (586 mg, Yield: 100%) as nearly colorless oily products.
IR (neat): 1745, 835 cm⁻¹.
NMR δ (CDCl₃): 6.25 (d, J=16 Hz, ½H, trans), 6.01 (d, J=11Hz, ⅜H, cis), 5.50 (m, 4H), 4.07 (m, 1H), 3.69 (m, 1H), 3.68 (s, 3H).
Mass m/z: 588, 532, 531, 517.
[α]$_D^{20}$=−37° (c=1.62, CHCl₃).

REFERENCE EXAMPLE 46

{3-(4'-Methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (70 mg, 0.19 mmol) was dissolved in DMF (0.25 ml). With addition of t-butyldimethylsilylchloride (85 mg, 0.57 mmol) and imidazole (38 mg, 0.57 mmol), the mixture was stirred at room temperature for 2 hours. The reaction was stopped by adding a saturated aqueous ammonium chloride solution and the mixture was extracted with ether. The separated ether layer was washed with a saturated saline solution and dried with anhydrous magnesium sulfate. The solvent was distilled out and the residue was purified through silica gel column chromatography to obtain {3-(4'-methoxycarbonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene} (93 mg, Yield: 82%) as nearly colorless oily products.
IR (neat): 1745, 840 cm⁻¹.
NMR δ (CDCl₃): 6.23, 5.97 (each d, J=15 Hz, J=11Hz, 1H), 5.05–5.70 (m, 4H,), 3.65 (s, 3H), 1.75 (t, J=2 Hz, 3H).
Mass m/z: 600, 543.
[α]$_D^{20}$=−30° (c=1.82, CHCl₃).

REFERENCE EXAMPLE 47

The reaction was carried out following the same procedures as in Reference example 46 except for using {3-(4'-methoxycarbonyl-1'-butenyl)-6(S)-(3'(S)-hydroxy-5'(R)-methyl-9'-methyl-trans-1'-decen-8'-enyl)-7(R)-hydroxy-(1S,5S)-cis-bicyclo-[3.3.0]oct-2-ene} (90 mg, 0.22 mmol) to obtain {3-(4'-methoxycarbonyl-1'-butenyl)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cis-bicyclo[3.3.-0]oct-2-ene} (108 mg, Yield: 78%) as nearly colorless oily products.
IR (neat): 1745, 835 cm⁻¹.
NMR δ (CDCl₃): 6.20, 5.95 (each d, J=15 Hz, J=11Hz, 1H), 5.00–5.60 (m, 5H), 3.68 (s, 3H), 1.66 (s, 3H), 1.60 (s, 3H).
Mass m/z: 644, 587, 519.
[α]$_D^{20}$=−45° (c=2.18, CHCl₃).

REFERENCE EXAMPLE 48

The reaction was carried out following the same procedures as in Reference example 44 except for using {3-(4'-ethoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (187 mg, 0.5 mmol) to obtain {3-(4'-ethoxycarbonyl-1'-butenyl)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]oct-2-ene} (286 mg, Yield: 95%) as colorless oily products.
IR (neat): 1745 cm⁻¹.
NMR δ (CDCl₃): 6.25 (d, J=16 Hz, ½H, trans), 6.01 (d, J=11Hz, ⅜H, cis), 5.50 (m, 4H), 4.20 (q, J=7 Hz, 2H), 4.07 (m, 1H), 3.69 (m, 1H), 1.30 (t, J=7 Hz, Mass m/z: 602, 545.

REFERENCE EXAMPLE 49

The reaction was carried out following the same procedures as in Reference example 44 except for using {3-(4'-ethoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (193 mg, 0.5 mmol) to obtain {3-(4'-ethoxycarbonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene} (300 mg, Yield: 100%) as nearly colorless oily products.
IR (neat): 1745 cm⁻¹.
NMR δ (CDCl₃): 6.25 (d, J=16 Hz, ½H, trans), 6.01 (d, J=11Hz, ⅜H, cis), 5.50 (m, 4H), 4.20 (q, J=7 Hz, 2H), 4.07 (m, 1H), 3.69 (m, 1H), 1.75 (t, J=2 Hz, 3H), 1.30 (t, J=7 Hz, 3H), 1.20 (d, J=7 Hz, 3H).
Mass m/z: 614, 557.

REFERENCE EXAMPLE 50

The reaction was carried out following the same procedures as in Reference example 50 except for using {3-(4'-ethoxycarbonyl-1'-butenyl)-6(S)-(3'(S)-hydroxy-5'(R)-methyl-9'-methyl-trans-1'-decen-8'-enyl)-7(R)-hydroxy-(1S,5S)-cis-bicyclo[3.3.0]-oct-2-ene} (95 mg, 0.22 mmol) obtain {3-(4'-ethoxycarbonyl-1'-butenyl)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cisbicyclo[3.3.0]oct-2-ene} (145 mg, Yield: 100%) as nearly colorless oily products.
IR (neat): 1743 cm⁻¹.
NMR δ (CDCl₃): 6.20, 5.95 (each d, J=15 Hz, J=11Hz, 1H), 5.00–5.60 (m, 5H), 4.20 (q, J=7 Hz, 2H), 1.66 (s, 3H), 1.60 (s, 3H), 1.30 (t, J=7 Hz, 3H).
Mass m/z: 658, 601, 533.

REFERENCE EXAMPLE 27

In methylene chloride (3.6 ml) was dissolved {3-(4'-methoxycarbonyl-1'-butenyl)-6(S)-(3'(S)-hydroxy-trans-1'-octenyl)-7(R)-hydroxy-(1S,5S)-cis-bicyclo[3.3.-0]oct-2ene} (362 mg, 1 mmol). Dihydropyrane (840 mg, 10 mmol) was added to the resultant solution and catalytic amount of p-toluenesulfonic acid was further added to the mixture, followed by stirring at room temperature for 10 minutes. The reaction was stopped by addition of a saturated aqueous sodium hydrogencarbonate solution and the mixture was extracted with ether. The separated ether layer was washed with a saturated saline solution, followed by dryness with anhydrous magnesium sulfate. After the solvent was distilled out, the residue was purified through silica gel column chromatography to obtain {3-(4'-methoxycarbonyl-1'-butenyl)-6(S)-(3'(S)-tetrahydropyranyloxy-trans-1'-octenyl)-7(R)-tetrahydropyranyloxy-(1S,5S)-cis-bicyclo[3.3.0]oct-2-ene} (477 mg, Yield: 90%) as neary colorless oily products.

IR (neat): 1745 cm$^{-1}$.

NMR δ (CDCl$_3$): 6.25 (d, J=16 Hz, ½H, trans), 6.02 (d, J=11Hz, ⅔H, cis), 5.50 (m, 4H), 4.60 (m, 2H), 4.05 (m, 1H), 3.69 (s, 3H), 3.40–4.00 (m, 5H).

Mass m/z: 530, 446.

REFERENCE EXAMPLE 52

The reaction was carried out following the same procedures as in Reference example 51 except for using {3-(4'-methoxycarbonyl-1'-butenyl)-6(S)-(3'(S)-hydroxy-3'-cyclopentyl-trans-1'-propenyl)-7(R)-hydroxy-(1S,5S)-cis-bicyclo[3.3.0]oct-2-ene} (360 mg, 1 mmol) to obtain {3-(4'-methoxycarbonyl-1'-butenyl)-6(S)-(3'(S)-tetrahydropyranyloxy-3'-cyclopentyl-trans-1'-propenyl)-7(R)-tetrahydropyranyloxy-(1S,5S)-cis-bicyclo[3.3.0]oct-2-ene} (475 mg, Yield: 90%) as colorless oily products.

IR (neat): 1745 cm$^{-1}$.

NMR δ (CDCl$_3$): 6.23 (d, J=16 Hz, ½H, trans), 6.03 (d, J=11Hz, ⅔H, cis), 5.50 (m, 4H), 4.60 (m, 2H), 4.05 (m, 1H), 3.68 (s, 3H), 3.40–4.00 (m, 5H).

Mass m/z: 528, 444.

REFERENCE EXAMPLE 53

{3-(4'-Methoxycarbonyl-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (186 mg, 0.5 mmol) was dissolved in methylene chloride (1.86 ml). Dihydropyrane (420 mg, 5 mmol) was added to the resultant solution and catalytic amount of p-toluenesulfonic acid was further added to the mixture, followed by stirring at room temperature for 10 minutes. The reaction was stopped by addition of a saturated aqueous sodium hydrogencarbonate solution and the mixture was extracted with ether. The separated ether layer was washed with a saturated saline solution, followed by dryness with anhydrous magnesium sulfate. After the solvent was distilled out, the residue was purified through silica gel column chromatography to obtain (3-(4'-methoxycarbonyl-1'-butenyl)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.0]oct-2-ene} (256 mg, Yield: 95%) as neary colorless oily products.

IR (neat): 1743 cm$^{-1}$.

NMR δ (CDCl$_3$): 6.23 (d, J=16 Hz, ½H, trans), 6.03, (d, J=11Hz, ⅔H, cis), 5.50 (m, 4H), 4.60 (m, 2H), 4.05 (m, 1H), 3.67 (s, 3H), 3.40–4.00 (m, 5H), 1.75 (t, J=2 Hz, 3H), 1.20 (d, J=7 Hz, 3H).

Mass m/z: 538, 454.

REFERENCE EXAMPLE 54

The reaction was carried out following the same procedures as in Reference example 53 except for using {3-(4'-methoxycarbonyl-1'-butenyl)-6(S)-(3'(S)-hydroxy-5'(R)-methyl-9'-methyl-trans-1'-decen-8'-enyl)-7(R)-hydroxy(1S,5S)-cis-bicyclo[3.3.0]oct-2-ene} (208 mg, 0.5 mmol) to obtain {3-(4'-methoxycarbonyl-1-'-butenyl)-6(S)-(3'(S)-tetrahydropyranyloxy-5'(R)-methyl-9'-methyl-trans-1'-decen-8'-menyl)-7(R)-tetrahydropyranyloxy-(1S,5S)-cisbicyclo[3.3.0]oct-2-ene} (274 mg, Yield: 94%) as nearly colorless oily products.

IR (neat): 1745 cm$^{-1}$.

NMR δ (CDCl$_3$): 6.26, 6.00 (each d, J=15 Hz, J=11Hz, 1H), 5.00–5.62 (m, 5H), 4.65 (2H, m), 3.70 (s, 3H), 0.93 (d, J=6 Hz, 3H).

Mass m/z: 582, 498.

EXAMPLE 12

In acetone (10 ml) were dissolved {3-(4'-methoxycarbonyl-1'-butenyl)-6(S)-(3'(S)-t-butyldimethylsilyloxy-3'-cyclopentyl-trans-1'-propenyl-7(R)-t-butyldimethylsilyloxy-(1S,5S)-cis-bicyclo[3.3.0]oct-2-ene} (cis:trans=2:1 mixture; 105 mg, 0.18 mmol) and methylbezoatetricarbonyl chromium (9 mg, 0.03 mmol) and the solution was degassed. In an autoclave under 70 Kg/cm$^2$ of hydrogen gas pressure, the reaction was carried out at 120° C. for 15 hours. The solvent was distilled out and the residue was purified through silica gel column chromatograpy to obtain {3(E)-(4'-methoxycarbonylbutylidene)-6(S)-(3'(S)-t-butyldimethylsilyloxy- 3'-cyclopentyl-trans-1'-propenyl)-7(R)-t-butyldimethylsilyloxy-(1S,5S)-cis-bicyclo[3.3.0]octane} (105 mg, Yield: 100%) as nearly colorless oily products.

IR (neat): 1745 cm$^{-1}$.

NMR δ (CDCl$_3$): 5.50 (m, 2H), 5.23 (t, J=7 Hz, 1H), 3.68 (s, 3H), 3.50–4.00 (m, 2H).

Mass m/z: 533, 521.

Results are summarized in the following Table 1 in which solvents and catalysts other than the above-mentioned were used.

TABLE 1

| Solvent | Catalyst | Amount of catalyst (wt. %) | Hydrogen pressure (Kg/cm$^2$) | Temperature (°C.) | Reaction time (hour) | Yield (%) |
|---|---|---|---|---|---|---|
| acetone | toluenetricarbonyl chromium | 20 | 70 | 130 | 13 | 82* |
| acetonitrile | methylbezoatetricarbonyl chromium | 20 | 70 | 130 | 12 | 21* |
| acetone | mesitylenetricarbonyl molybdenum | 20 | 70 | 100 | 12 | 52* |
| acetone | mesitylenetricarbonyl tungsten | 20 | 70 | 120 | 12 | 12* |
| acetone | triphenylphosphinpentacarbonyl chromium | 20 | 70 | 180 | 15 | 9* |
| acetone | Hydridecyclopentadienyltricarbonyl | 10 | 90 | 100 | 15 | 50° |

| Solvent | Catalyst | Amount of catalyst (wt. %) | Hydrogen pressure (Kg/cm$^2$) | Temperature (°C.) | Reaction time (hour) | Yield (%) |
|---|---|---|---|---|---|---|
| | chromium | | | | | |

*Selectivity coefficient of E-isomer was 100%.

EXAMPLE 13

The reaction was carried out following the same procedures as in Example 12 except for using {3-(4'-methoxycarbonyl-1'-butenyl)-6(S)-(3'(S)-tetrahydropyranyloxy-3'-cyclopentyl-trans-1'-propenyl)-7(R)-tetrahydropyranyloxy-1S,5S)-cis-bicyclo[3.3.0]oct-2-ene} (cis:trans=2:1 mixture; 111 mg, 0.21 mmol) to obtain {3(E)-(4'-methoxycarbonylbutylidene)-6(S)-(3'(S)-tetrahydropyranyloxy-3'-cyclopentyl-trans-1'-propenyl)-7(R)-tetrahydropyranyloxy-(1S,5S)-cis-bicyclo[3.3.0]octane} (100 mg, Yield: 90%) as nearly colorless oily product.

IR (neat): 1744 cm$^{-1}$.

NMR δ (CDCl$_3$): 5.48 (m, 2H), 5.23 (t, J=7 Hz, 1H), 4.60 (m, 2H), 3.68 (s, 3H), 3.40–4.00 (m, 6H).

Mass m/z: 530, 461, 446.

EXAMPLE 14

In acetone (10 ml) were dissolved {3-(4'-methoxycarbonyl-1'-butenyl)-6(S)-(3'(S)-t-butyldimethylsilyloxy-trans-1'-octenyl)-7(R)-t-butyldimethylsilyloxy-(1S,5S)-cis-bicyclo[3.3.0]oct-2-ene} (cis:trans=2:1 mixture; 107 mg, 0.18 mmol) and methylbenzoatetricarbonyl chromium (9 mg, 0.03 mmol) and the solution was degassed. In an autoclave under 70 Kg/cm$^2$ of hydrogen gas pressure, the reaction was carried out at 120° C. for 15 hours. The solvent was distilled out and the residue was purified through silica gel column chromatography to obtain {3(E)-(4'-methoxycarbonylbutylidene)-6(S)-(3'(S)-t-butyldimethylsilyloxy-trans-1'-octenyl)-7(R)-t-butyldimethylsilyloxy-(1S,5S)-cis-bicyclo[3.3.0]octane} (107 mg, 100%) as nearly colorless oily products.

IR (neat): 1745 cm$^{-1}$.

NMR δ (CDCl$_3$): 5.50 (m, 2H), 5.23 (t, J=7 Hz, 1H), 3.68 (s, 3H), 3.50–4.00 (m, 2H).

Mass m/z: 535.

EXAMPLE 15

The reaction was carried out following the same procedures as in Example 14 except for using {3-(4'-methoxy-carbonyl-1'-butenyl)-6(S)-(3'(S)-tetrahydropyranyloxy-trans-1'-octenyl)-7(R)-tetrahydropyranyloxy-(1S,5S)-cis-bicyclo[3.3.0]oct-2-ene} (cis:trans=2:1 mixture; 112 mg, 0.21 mmol) to obtain }3(E)-(4'-methoxycarbonylbutylidene)-6(S)-(3'(S)-tetrahydropyranyloxy-trans-1'-octenyl)-7(R)-tetrahydropyranyloxy-(1S,5S)-cis-bicyclo[3.3.0]octane} (101 mg, Yield: 90%) as nearly colorless oil products.

IR (neat): 1744 cm$^{-1}$.

NMR δ (CDCl$_3$): 5.48 (m, 2H), 5.23 (t, J=7 Hz, 1H), 4.60 (m, 2H), 3.68 (s, 3H), 3.40–4.00 (m, 6H).

Mass m/z: 532, 448.

EXAMPLE 16

In acetone (10 ml) were dissolved {3-(4'-ethoxycarbonyl-1'-butenyl)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]oct-2-ene} (cis:trans=2:1 mixture; 108 mg, 0.18 mmol) and methylbenzoatetricarbonyl chromium (9 mg, 0.03 mmol) and the solution was degassed. In an autoclave under 70 Kg/cm$^2$ of hydrogen pressure, the reaction was carried out at 120° C. for 15 hours. The solvent was distilled out and the residue was purified through silica gel column chromatography to obtain {3(E)(4'-ethoxycarbonylbutylidene)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]octane} (108 mg, Yield: 100%) as nearly colorless oily product.

IR (neat): 1745 cm$^{-1}$.

NMR δ (CDCl$_3$): 5.50 (m, 2H), 5.23 (t, J=7 Hz, 1H), 4.20 (q, J=7 Hz, 2H), 3.50–4.00 (m, 2H), 1.30 (t, J=7 Hz, 3H).

Mass m/z: 604, 547, 535.

EXAMPLE 17

In acetone (10 ml) were dissolved {3-(4'-methoxycarbonyl-1'-butenyl)-6(S)-(3'(S)-t-butyldimethylsilyloxy-5'(R)-methyl-9'-methyl-trans-1'-decen-8'-enyl)-7(R)-t-butyldimethylsilyloxy-(1S, 5S)-cis-bicyclo[3.3.0]oct-2-ene} (cis:trans=2:1 mixture; 116 mg, 0.18 mmol) and methylbenzoatetricarbonyl chromium (9 mg, 0.03 mmol) and the solution was degassed. In an autoclave under 70 Kg/cm$^2$ of hydrogen pressure, the reaction was carried out at 120° C. for 15 hours. The solvent was distilled out and the residue was purified through silica gel column chromatography to obtain {3(E)-(4'-methoxycarbonylbutylidene)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cis-bicyclo[3.3.0]octane} (105 mg, Yield: 90%) as nearly colorless oily product.

IR (neat): 1745 cm$^{-1}$.

NMR δ (CDCl$_3$): 5.50 (m, 2H), 5.18 (m, 2H), 3.70 (s, 3H), 1.74 (s, 3H), 1.62 (s, 3H).

Mass m/z: 646, 589.

EXAMPLE 18

The reaction was carried out following the same procedures as in Example 17 except for using {3-(4'--methoxycarbonyl-1'-butenyl)-6(S)-(3'(S)-tetrahydropyranyloxy-5'(R)-methyl-9'-methyl-trans-1'-decen-8'-enyl)-7(R)-tetrahydropyranyloxy-(1S,5S)-cis-bicyclo[3.3.0]oct-2ene} (cis:trans=2:1 mixture; 105 mg, 0.18 mmol) to obtain {3(E)-(4'-methoxycarbonylbutylidene)-6(S)-(3(S)-tetrahydropyranyloxy-5'(R)-methyl-9'-methyl-trans-1'-decen-8'-enyl)-7(R)-tetrahydropyranyloxy-(1S,5S)-cis-bicyclo[3.3.0]octane} (89 mg, Yield: 85%) as nearly colorless oil product.

IR (neat): 1743 cm$^{-1}$.

NMR δ (CDCl$_3$): 5.50 (m, 2H), 5.21 (m, 2H), 4.60 (m, 2H), 3.66 (s, 3H), 3.30–4.10 (m, 6H), 0.93 (d, J=6 Hz, 3H).

Mass m/z: 584, 500.

EXAMPLE 19

In acetone (10 ml) were dissolved {3-(4'-methoxycarbonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene} (cis:trans=2:1 mixture; 92 mg, 0.16 mmol) and methylbenzoatetricarbonyl chromium (9 mg, 0.03 mmol) and the solution was degassed. In an autoclave under 70

Kg/cm² of hydrogen gas pressure, the reaction was carried out at 120° C. for 15 hours. The solvent was distilled out and the residue was purified through silica gel column chromatography to obtain {3(E)-(4'-methoxycarbonylbutylidene)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene} (38 mg, Yield: 41%) as nearly colorless oily product.

IR (neat): 1745 cm$^{-1}$.

NMR δ (CDCl$_3$): 5.45 (m, 2H), 5.20 (t, J=7 Hz, 1H), 3.62 (s, 3H), 1.74 (t, J=2 Hz, 3H).

Mass m/z: 602, 545.

Results are summarized in the following Table 2 in which solvents and catalysts other than the above-mentioned were used.

TABLE 2

| Solvent | Catalyst | Amount of catalyst (wt. %) | Hydrogen pressure (Kg/cm²) | Temperature (°C.) | Reaction time (hour) | Yield (%) |
| --- | --- | --- | --- | --- | --- | --- |
| acetone | toluene-tricarbonyl chromium | 20 | 70 | 130 | 13 | 31* |
| acetonitrile | methylbezoatetricarbonyl chromium | 20 | 70 | 130 | 12 | 5* |
| acetone | mesitylene-tricarbonyl molybdenum | 20 | 70 | 100 | 12 | 26* |
| acetone | mesitylene-tricarbonyl tungsten | 20 | 70 | 120 | 12 | 5* |
| acetone | triphenyl-phosphin-pentacarbonyl chromium | 20 | 70 | 180 | 15 | 4* |
| acetone | Hydridecyclo-pentadienyl-tricarbonyl chromium | 10 | 90 | 100 | 15 | 21* |

*Selectivity coefficient of E-isomer was 100%.

EXAMPLE 20

The reaction was carried out following the same procedures as in Example 17 except for using {3-(4'-methoxycarbonyl-1'-butenyl)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cis-bicyclo[3.3.0]oct-2-ene} (cis:trans=2:1 mixture; 118 mg, 0.18 mmol) to obtain {3(E)-(4'-ethoxycarbonylbutylidene)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cis-bicyclo[3.3.0]octane} (107 mg, Yield: 90%) as nearly colorless oily product.

IR (neat): 1745 cm$^{-1}$.

NMR δ (CDCl$_3$): 5.50 (m, 2H), 5.23 (m, 2H), 4.20 (q, J=7 Hz, 2H), 1.70 (s, 3H), 1.62 (s, 3H), 1.30 (t, J=7 Hz, 3H).

Mass m/z: 660, 503.

EXAMPLE 21

The reaction was carried out following the same procedures as in Example 19 except for using {3-(4'-methoxycarbonyl-1'-butenyl)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.0]oct-2-ene} (cis:trans=2:1 mixture; 86 mg, 0.16 mmol) to obtain {3(E)-(4'-methoxycarbonylbutylidene)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.0]octane} (26 mg, Yield: 30%) as nearly colorless oily product.

IR (neat): 1745 cm$^{-1}$.

NMR δ (CDCl$_3$): 5.48 (m, 2H), 5.23 (t, J=7 Hz, 1H), 4.60 (m, 2H), 3.70 (s, 3H), 1.75 (t, J=2 Hz, 3H).

Mass m/z: 540, 456.

EXAMPLE 22

The reaction was carried out following the same procedures as in Example 19 except for using {3-(4'-ethoxycarbonyl-1'-butenyl)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]oct-2-ene} (cis:trans=2:1 mixture; 98 mg, 0.16 mmol) to obtain {3(E)-(4'-ethoxycarbonylbutylidene)-6(S)-(3'(S)-t-butyldimethylsilyloxy-4'(RS)-methyl-trans-1'-octen-6'-ynyl)-7(R)-t-butyldimethysilyloxy-(1S,5S)-cis-bicyclo[3.3.0]octane} (39 mg, Yield:40%) as nearly colorless oily product.

IR (neat):1745 cm$^{-1}$.

NMR δ (CDCl$_3$): 5.48 (m, 2H), 5.23 (t, J=7 Hz, 1H) 4.20 (q, J=7 Hz, 2H), 1.75 (t, J=2 Hz, 3H), 1.30 (t, J=7 Hz, 3H).

Mass m/zn: 616, 559.

EXAMPLE 23

The reaction was carried out following the same procedures as in Example 19 except for using {3-(4'-carboxy-1'-butenyl)-6(S)-(3'(S)-hydroxy-4'(RS)-methyl-trans-1'-octen-6'-ynyl)-7(R)-hydroxy-(1S,5S)-cis-bicyclo[3.3.0]oct-2-ene} (cis:trans=2:1 mixture; 36 mg, 0.100 mmol) to obtain {3(E)-(4'-carboxybutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (6 mg, Yield: 18%) as viscous colorless oily products.

Each spectrum data of the obtained product agreed with those of the product obtained in Reference example 68.

EXAMPLE 24

The reaction was carried out following the same procedures as in Example 17 except for using {3-(4'-carboxy-1'-butenyl)-6(S)-(3'(S)-hydroxy-5'(R)-methyl-9'-methyl-trans-1'-decen-8'-enyl)-7(R)-hydroxy-(1S,5S)-cis-bicyclo-[3.3.0]oct-2-ene} (20 mg, 0.05 mmol) (cis:trans=2:1 mixture) to obtain {3(E)-(4'-carboxybutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (14 mg, Yield: 68%) as viscous colorless oily products.

Each spectrum data of the obtained product agreed with those of the compound obtained in Reference example 70.

REFERENCE EXAMPLE 55

In THF (1.5 ml) was dissolved {3(E)-(4'-methoxycarbonylbutylidene)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]octane} (93 mg, 0.16 mmol). To the thus prepared mixture was added a THF solution of tetrabutylammonium fluoride (0.48 mmol, 1M THF solution), followed by stirring at room temperature for 12 hours. A saturated saline solution was added to the mixture and the mixture was extracted with ethyl acetate. After the separated organic layer was dried with anhydrous magnesium sulfate, the solvent was distilled out and the residue was purified through silica gel column chromatography to obtain {3(E)-(4'-methoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (47 mg, Yield: 82%) as colorless viscous liquid. The product solidified when allowed to stand.

IR (neat): 3400, 1742 cm$^{-1}$.

NMR $\delta$ (CDCl$_3$): 5.50 (m, 2H), 5.20 (t, J=7 Hz, 1H), 3.67 (s, 3H), 3.50–3.90 (m, 2H).

Mass m/z: 344, 326.

REFERENCE EXAMPLE 56

In THF (0.13 ml) was dissolved {3(E)-(4'-methoxycarbonylbutylidene)-6(S)-(3'(S)-tetrahydropyranyloxy-3'-cyclopentyl-trans-1'-propenyl)-7(R)-tetrahydropyranyloxy-(1S,5S)-cis-bicyclo[3.3.0]octane} (53 mg, 0.1 mmol). A 65% aqueous acetic acid solution (1.3 ml) was added to the thus prepared solution, followed by stirring at 50° C. for 2 hours. The mixture was poured into a cooled saturated aqueous sodium hydrogencarbonate solution, and the mixture was extracted with ethyl acetate. After the separated organic layer was dried with anhydrous magnesium sulfate and the solvent was distilled out, the residue was purified through silica gel column chromatography to obtain {3(E)-(4'-methoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (33 mg, Yield: 90%) as colorless viscous liquid. The product solidified when allowed to stand. Each spectrum data of the obtained product accorded completely with those obtained in Reference example 55.

REFERENCE EXAMPLE 57

The reaction was carried out following the same procedures as in Reference example 55 except for using {3(E)-(4'-methoxycarbonylbutylidene)-6(S)-(3'(S)-t-butyldimethylsilyloxy-trans-1'-octenyl)-7(R)-t-butyldimethylsilyloxy-(1S,5S)-cis-bicyclo[3.3.0]octane} (94 mg, 0.16 mmol) to obtain {3(E)-(4'-methoxycarbonylbutylidene)-6(S)-(3'(S)-hydroxy-trans-1'-octenyl)-7(R)-hydroxy-(1S,5S)-cis-bicyclo[3.3.0]octane} (52 mg, Yield: 90%) as nearly colorless viscous oily product.

IR (neat): 3370, 1740 cm$^{-1}$.

NMR $\delta$ (CDCl$_3$):5.49 (m, 2H), 5.23 (t, J=7 Hz, 1H), 3.66 (s, 3H), 3.55–4.05 (m, 2H).

Mass m/z:346, 328.

The above values completely accorded with those described in the Reference (M. Hayashi, et al., Tetrahedron, 37, 4391 (1981)). In the above-mentioned reference, {3(E)-(4'-methoxycarbonylbutylidene)-6(S)-(3'(S)-hydroxy-trans-1'-octenyl)-7(R)-hydroxy-cis-bicyclo[3.3.0]octene} was led to carbacycline.

REFERENCE EXAMPLE 58

The reaction was carried out following the same procedures as in Reference example 56 except for using {3(E)-(4'-methoxycarbonylbutylidene)-6(S)-(3'(S)-tetrahydropyranyloxy-trans-1'-octenyl)-7(R)-tetrahydropyranyloxy-(1S,5S)-cis-bicyclo[3.3.0]octane} (54 mg, 0.1 mmol) to obtain {3(E)-(4'-methoxycarbonylbutylidene)-6(S)-(3'(S)-hydroxy-trans-1'-octenyl)-7(R)-hydroxy-(1S,5S)-cis-bicyclo[3.3.0]octane} (34 mg, Yield:90%) as nearly colorless viscous oily product. Each spectrum data of the obtained product completely accorded with those obtained in Reference example 57.

REFERENCE EXAMPLE 59

The reaction was carried out following the same procedures as in Reference example 55 except for using {3(E)-(4'-ethoxycarbonylbutylidene)-6(S)-(3'(S)-t-butyldimethylsilyloxy-3'-cyclopentyl-trans-1'-propenyl)-7(R)-t-butyldimethylsilyloxy-(1S,5S)-cis-bicyclo[3.3.0]octane} (60 mg, 0.1 mmol) to obtain {3(E)-(4'-ethoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (36 mg, Yield:100%) as colorless viscous oily product.

The product solidified when allowed to stand.

IR (neat): 3400, 1742 cm$^{-1}$.

NMR $\delta$ (CDCl$_3$): 5.50 (m, 2H), 5.20 (t, J=7Hz, 1H), 4.20 (q, J=7 Hz, 2H), 3.50–3.95 (m, 2H), 1.30 (t, J=7 Hz, 3H).

Mass m/z: 358, 340.

REFERENCE EXAMPLE 60

The reaction was carried out following the same procedures as in Reference example 55 except for using {3(E)-(4'-methoxycarbonylbutylidene)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cis-bicyclo-[3.3.0]octane} (103 mg, 0.16 mmol) to obtain {3(E)-(4'-methoxycarbonylbutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (60 mg, Yield: 90%) as nearly colorless oily product.

IR (neat): 3400, 1742 cm$^{-1}$.

NMR $\delta$ (CDCl$_3$): 5.50 (m, 2H), 5.20 (m, 2H), 3.67 (s, 3H), 3.50–3.90 (m, 2H), 0.93 (d, J=6 Hz, 3H).

Mass m/z: 418, 400, 382.

REFERENCE EXAMPLE 61

The reaction was carried out following the same procedures as in Reference example 60 except for using {3(E)-(4'-methoxycarbonylbutylidene)-6(S)-(3'(S)-tetrahydropyranyloxy-5'(R)-methyl-9'-methyl-trans-1'-decen-8'-enyl)-7(R)-tetrahydropyranyloxy-(1S,5S)-cis-bicyclo[3.3.0]octane} (93 mg, 0.16 mmol) to obtain {3(E)-(4'-methoxycarbonylbutylidene)-6(S)-(3'(S)-hydroxy-5'(R)-methyl-9'-methyl-trans-1'-decene-8'-enyl)-7(R)-hydroxy-(1S,5S)-cis-bicyclo[3.3.0]octane} (60 mg, Yield: 90%) as nearly colorless oily product.

Each spectrum data of the obtained product completely accorded with those obtained in Reference example 60.

REFERENCE EXAMPLE 62

The reaction was carried out following the same procedures as in Reference example 60 except for using {3(E)-(4'-ethoxycarbonylbutylidene)-6(S)-(3'(S)-t-butyldimethylsilyloxy-5'(R)-methyl-9'-methyl-trans-1'-decen-8'-enyl)-7(R)-t-butyldimethylsilyloxy-(1S,5S)-cis-bicyclo[3.3.0]octane} (66 mg, 0.1 mmol) to obtain {3(E)-(4'-ethoxycarbonylbutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (43 mg, Yield: 100%) as nearly colorless oily products.

IR (neat): 3400, 1742 cm$^{-1}$.

NMR δ (CDCl$_3$): 5.50 (m, 2H), 5.20 (m, 2H), 4.20 (q, J=7 Hz, 2H), 3.50–3.90 (m, 2H), 1.30 (t, J=7 Hz, 3H), 0.93 (d, J=6 Hz, 3H).

Mass m/z: 430, 412, 394.

REFERENCE EXAMPLE 63

The reaction was carried out following the same procedures as in Reference example 55 except for using {3(E)-(4'-methoxycarbonylbutylidene)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]-octane} (120 mg, 2 mmol) to obtain {3(E)-(4'-methoxycarbonylbutylidene)-6(S)-(3'(S)-hydroxy-4'(RS)-methyltrans-1'-octen-6'-ynyl)-7(R)-hydroxy-(1S,5S)-cis-bicyclo-[3.3.0]octane} (71 mg, Yield: 95%) as nearly colorless oily product.

IR (neat): 3400, 1742 cm$^{-1}$.

NMR δ (CDCl$_3$): 5.50 (m, 2H), 5.20 (t, J=7 Hz, 1H), 3.67 (s, 3H), 1.75 (t, J=2 Hz, 3H), 1.20 (d, J=7 Hz, 3H).

Mass m/z: 374, 356.

REFERENCE EXAMPLE 64

The reaction was carried out following the same procedures as in Reference example 56 except for using {3(E)-(4'-methoxycarbonylbutylidene)-6(S)-(3'(S)-tetrahydropyranyloxy-4'(RS)-methyl-trans-1'-octen-6'-ynyl)-7(R)-tetrahydropyranyloxy-(1S,5S)-cis-bicyclo[3.3.0]octane} (54 mg, 0.1 mmol) to obtain {3(E)-(4'-methoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]-octane} (37 mg, Yield: 100%) as nearly colorless oily product. Each spectrum data thereof completely accorded with those obtained in Reference example 62.

REFERENCE EXAMPLE 65

The reaction was carried out following the same procedures as in Reference example 55 except for using {3-(E)-(4'-ethoxycarbonylbutylidene)-6(S)-(3'(S)-t-butyldimethylsilyloxy-4'(RS)-methyl-trans-1'-octen-6'-ynyl)-7(R)-t-butyldimethylsilyloxy-(1S,5S)-cis-bicyclo[3.3.0]octane} (62 mg, 0.1 mmol) to obtain {3(E)-(4'-ethoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]-octane} (39 mg, Yield: 100%) as nearly colorless oily product.

IR (neat): 3400, 1742 cm$^{-1}$.

NMR δ (CDCl$_3$): 5.50 (m, 2H), 5.20 (t, J=7 Hz, 1H), 4.20 (q, J=2 Hz, 3H), 1.75 (t, J=2 Hz, 3H), 1.30 (t, J=7 Hz, 3H), 1.20 (d, J=7 Hz, 3H).

Mass m/z: 388, 370.

REFERENCE EXAMPLE 66

In methanol (1 ml) was dissolved {3(E)-(4'-methoxycarbonylbutylidene)-6(S)-(3'(S)-hydroxy-3'-cyclopentyl-trans-1'-propenyl)-7(R)-hydroxy-(1S,5S)-cis-bicyclo[3.3.0]octane} (45 mg, 0.12 mmol). A 10% aqueous sodium hydroxide solution (0.5 ml) was added to the thus prepared solution, followed by stirring at 0° C. for 13 hours. The reaction mixture was diluted with ether, and neutralized with a 10% aqueous hydrochloric acid solution. Then, methanol and ether were distilled out under reduced pressure. The resultant aqueous layer was adjusted to pH 4 to 5, and extracted with ethyl acetate. After the separated organic layer was dried with anhydrous magnesium sulfate, the solvent was distilled out to obtain {3(E)-(4'-carboxybutylidene)-6(S)-(3'(S)-hydroxy-3'-cyclopentyl-trans-1'-propenyl)-7(R)-hydroxy-(1S,5S)-cis-bicyclo[3.3.0]octane} (32 mg, Yield: 74%) as colorless viscous liquid. The product solidified when allowed to stand.

IR (neat): 3400, 1710 cm$^{-1}$.

NMR δ (CDCl$_3$): 5.54 (m, 2H), 5.24 (t, J=7 Hz, 1H), 3.50–4.00 (m, 2H).

Mass m/z: 348, 330, 312.

The thus obtained product is a carbacycline analogue. The usefulness thereof was described in '83 Inflammation Seminar—Prostaglandine Program Preliminary Text, p. 37, (Ono-Yakuhin-Kogyo-KK., Central Research Center, Akiyoshi Kawasaki).

REFERENCE EXAMPLE 67

The reaction was carried out following the same procedures as in Reference example 66 except for using {3(E)-(4'-ethoxycarbonylbutylidene)-6(S)-(3'(S)-hydroxy-3'(S)-hydroxy- 3'-cyclopentyl-trans-1'-propeneyl-7(R)-hydroxy-(1S,5S)-cis-bicyclo[3.3.0]octane} (45 mg, 0.12 mmol) to obtain {3(E)-(4'-carboxylbutylidene)-6(S)-(3'(S)-hydroxy-3'(S)-cyclopentyl-trans-1'-propenyl-7(R)-hydroxy-(1S,5S)-cis-bicyclo[3.3.0]octane} (33 mg, Yield: 80%) as white solid product. Each spectrum data thereof completely accorded with those obtained in Reference example 66.

REFERENCE EXAMPLE 68

The reaction was carried out following the same procedures as in Reference example 66 except for using {3(E)-(4'-methoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (45 mg, 0.12 mmol) to obtain {3(E)-(4'-carboxylbutylidene)-6(S)-(3'(S)-hydroxy-4'(RS)-methyltrans-1'-octen-6'-ynyl)-7(R)-hydroxy-(1S,5S)-cis-bicyclo[3.3.0]octane} (35 mg, Yield: 80%) as viscous colorless oily product.

IR (neat): 3350, 1710 cm$^{-1}$.

NMR δ (CDCl$_3$): 5.47 (m, 2H), 5.18 (t, J=7 Hz, 1H), 3.50–4.09 (m, 2H), 1.78 (m, 3H), 0.94 and 1.02 (d, J=6.5 Hz, 3H).

Mass m/z: 360, 342, 324.

The thus obtained product agreed with useful carbacycline analogues disclosed in "Angew. Chem. Int. Ed. Engl., 20, 1046 (1981)" by H. Vorbrüggen et al.

REFERENCE EXAMPLE 69

The reaction was carried out following the same procedures as in Reference example 66 except for using {3(E)-(4'-ethoxycarbonylbutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (47 mg, 0.12 mmol) to obtain {3(E)-( 4'-carboxylbutylidene)-6(S)-(3'(S)-hydroxy-4'(RS)-methyl-trans-1'-octen-6'-ynyl)-7(R)-hydroxy-(1S,5S)-cis-bicyclo[3.3.0]octane} (35 mg, Yield: 80%) as viscous colorless oily product. Each spectrum data thereof accorded with those obtained in Reference example 68.

REFERENCE EXAMPLE 70

The reaction was carried out following the same procedures as in Reference example 66 except for using {3(E)-(4'-methoxycarbonylbutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (50 mg, 0.12 mmol) to obtain {3(E)-(4'-carboxylbutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (39 mg, Yield: 80%) as viscous colorless oily products.

IR (neat): 3400, 1710 cm$^{-1}$.

NMR δ (CDCl$_3$): 5.50 (m, 2H), 5.20–5.30 (m, 2H), 4.14 (m, 1H), 3.70 (m, 1H), 1.70 (s, 3H), 1.62 (s, 3H), 0.95 (d, J=6 Hz, 3H).

Mass m/z: 404, 386, 368.

The thus obtained product is a carbacycline analogue. The usefulness thereof was described in '83 Inflammation Seminar—Prostaglandine Program Preliminary Text, Shinsaku Kobayashi, p. 37.

REFERENCE EXAMPLE 71

The reaction was carried out following the same procedures as in Reference example 68 except for using {3(E)-(4'-ethoxycarbonylbutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (50 mg, 0.12 mmol) to obtain {3(E)-(4'-carboxybutylidene)-6(S)-(3'(S)-hydroxy-5'(R)-methyl-9'-methyl-trans-1'-decen-8'-enyl)-7(R)-hydroxy-(1S,5S)-cis-bicyclo[3.3.0]octane} (39 mg, Yield: 80%) as viscous colorless oily product.

Each spectrum data thereof accorded with those obtained in Reference example 70.

We claim:

1. A method for preparing a cis-bicyclo[3.3.0]octylidene derivative represented by the formula:

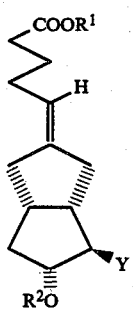

wherein R$^1$ is a hydrogen atom or an alkyl group; R$^2$ is a hydrogen atom or a protective group for hydroxyl group; and Y is

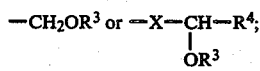

where R$^3$ is a hydrogen atom or a protective group for hydroxyl group; R$^4$ is a hydrogen atom or a straight, branched or cyclic alkyl group, alkenyl group or alkynyl group; and X is a group represented by CH=CH or C≡C, which comprises carrying out the catalytic hydrogenation reaction of a (1-alkenyl)-cis-bicyclo[3.3.0]octene derivative represented by the formula:

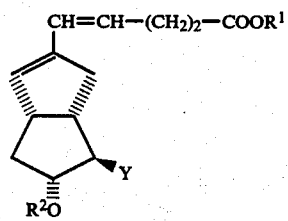

wherein R$^1$, R$^2$ and Y have the same meanings as defined above,
with hydrogen gas in the presence of a metal carbonyl compound or its complex represented by the formula:

wherein M is a metal element of the group VIB; R is a π ligand or a phosphine ligand; w is 1 or 2; x is an integer of 3 to 6; y is 0 or 1; and z is 0 or an integer of 1 to 3.

2. The method for preparing a cis-bicyclo[3.3.0]octylidene derivative according to claim 1, wherein said catalytic hydrogenation reaction is carried out at atmospheric pressure to 150 atm.

3. The method for preparing a cis-bicyclo[3.3.0]octylidene derivative according to claim 1, wherein said catalytic hydrogenation reaction is carried out at 30 to 150 atm.

4. The method for preparing a cis-bicyclo[3.3.0]octylidene derivative according to claim 1, wherein said catalytic hydrogenation reaction is carried out at room temperature to 200° C.

5. The method for preparing a cis-bicyclo[3.3.0]octylidene derivative according to claim 1, wherein an amount of the metal carbonyl compound or its complex is used in the range of 10$^{-5}$ to 20% by weight based on the (1-alkenyl)-cis-bicyclo[3.3.0]octene derivative.

6. The method for preparing a cis-bicyclo[3.3.0]octylidene derivative according to claim 1, wherein said catalytic hydrogenation reaction is carried out in the presence of a solvent.

7. The method for preparing a cis-bicyclo[3.3.0]octylidene derivative according to claim 6, wherein said solvent is selected from the group consisting of acetone, 2-butanone, 2-pentanone, 3-pentanone, acetonitrile, halogenated hydrocarbons, aromatic organic solvents, aliphatic hydrocarbons, esters, alcohols and tetrahydrofuran.

8. The method for preparing a cis-bicyclo[3.3.0]octylidene derivative according to claim 1, wherein said π ligand is selected from the group consisting of benzene, toluene, thiophene, pyridine, anisole, chlorobenzene, methyl benzoate, cyclopentadienyl, cyclopentadienylmethyl, cycloheptatriene, cyclooctatriene, mesitylene, stilbene, acetophenone, azulene, cyclooctadiene, 1,2-diphenylethane, diphenylmethane, biphenyl, 1,4-diphenylbutadiene, phenanthrene, 1,4-diphenyl-2,3-diethoxycarbonyl-2,5-cyclohexadiene, acetonitrile, hexamethylbenzene, 3-carbomethoxyanisole, benzophenone, bicyclo[2.2.1]hepta-2,5-diene, naphthalene and anthracene.

9. The method for preparing a cis-bicyclo[3.3.0]octylidene derivative according to claim 1, wherein at least one of $R^2$ and $R^3$ is selected from the group consisting of a tetrahydropyranyl group, a t-butyldimethylsilyl group, a 1-ethoxyethyl group, a diphenyl-t-butylsilyl group, a methoxymethyl group, a 1-methyl-1-methoxyethyl group, a 4-methoxytetrahydropyranyl group, a methyl group, a benzyl group, a benzoyl group, an acetyl group, a β-methoxyethoxymethyl group, and a triethylsilyl group.

* * * * *